(12) United States Patent
Keefe et al.

(10) Patent No.: US 10,093,970 B2
(45) Date of Patent: Oct. 9, 2018

(54) METHOD FOR SINGLE CELL ANALYSIS OF TELOMERE LENGTH USING PRE-AMPLIFICATION AND MULTIPLE-COPY REFERENCE SEQUENCE

(71) Applicants: New York University, New York, NY (US); Yale University, New Haven, CT (US)

(72) Inventors: David Keefe, New York, NY (US); Sherman Weissman, New Haven, CT (US); Lin Liu, Tampa, FL (US); Fang Wang, Rego Park, NY (US); Xinghua Pan, Hamden, CT (US)

(73) Assignees: New York University, New York, NY (US); Yale University, New Haven, CT (US)

( * ) Notice: Subject to any disclaimer, the term of this patent is extended or adjusted under 35 U.S.C. 154(b) by 301 days.

(21) Appl. No.: 14/776,384

(22) PCT Filed: Mar. 14, 2014

(86) PCT No.: PCT/US2014/027605
§ 371 (c)(1),
(2) Date: Sep. 14, 2015

(87) PCT Pub. No.: WO2014/152676
PCT Pub. Date: Sep. 25, 2014

(65) Prior Publication Data
US 2016/0032360 A1 Feb. 4, 2016

Related U.S. Application Data

(60) Provisional application No. 61/794,729, filed on Mar. 15, 2013.

(51) Int. Cl.
*C12P 19/34* (2006.01)
*C12Q 1/686* (2018.01)
*C12Q 1/6851* (2018.01)
*C12Q 1/6876* (2018.01)

(52) U.S. Cl.
CPC ........... *C12Q 1/686* (2013.01); *C12Q 1/6851* (2013.01); *C12Q 1/6876* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2003/0162266 A1 | 8/2003 | Cawthon |
| 2006/0003322 A1 | 1/2006 | Bentwich |
| 2006/0141451 A1 | 6/2006 | Keefe |
| 2010/0178655 A1 | 7/2010 | Hamilton et al. |
| 2011/0294676 A1 | 12/2011 | Cawthon |

OTHER PUBLICATIONS

Allshire, Robin C., et al., "Human telomeres contain at least three types of G-rich repeat distibuted non-randomly", Nucleic Acids Research (1989), vol. 17, No. 12, pp. 4611-4627.
Amit, Michal et al., "Clonally Derived Human Embryonic Stem Cell Lines Maintain Pluripotency and Proliferative Potential for Prolonged Periods of Culture", Developmental Biology (2000), vol. 227, pp. 271-278.
Aubert, Geraldine et al., "Telomere Length Measurement—caveats and a critical assessment of the available technologies arid tools", Mutat Res, (2012), vol. 730(1-2), pp. 59-67.
Baerlocher, Gabriela M., et al., "Telomere Length Measurements in Leukocyte Subsets by Automated Multicolor Flow-FISH", Original Articles, Cytometry Part A (2003), 55A, pp. 1-6.
Baird, Duncan M., et al., "Extensive allelic variation and ultrashort telomeres in senescent human cells", Nature Genetics (2003), vol. 33, pp. 203-207.
Blackburn, Elizabeth H., "Telomere states and cell fates", Nature (2000), vol. 408, pp. 53-56.
Blackburn, Elizabeth H., "Switching and Signaling at the Telomere", Cell (2001), vol. 106, pp. 661-673.
Britt-Compton, Bethun et al., "Structural stability and chromosome-specific telomere length is governed by cis-acting determinants in humans", Human Molecular Genetics (2006), vol. 15, No. 5, pp. 725-733.
Callicott, R. et al. "Real-time PCR Assay for Measurement of Mouse Telomeres", Comparative Med. (2006), vol. 56(1), pp. 17-22.
Canela, Andres et al., "High-throughput telomere length quantification by FISH and its application to human population studies", PNAS (2007), vol. 104, No. 13, pp. 5300-5305.
Cawthon, Richard M., "Telomere measurement by quantitative PCR", Nucleic Acids Research (2002), vol. 30, No. 10, p. e47 (1-6).
Cawthon, Richard M., "Telomere length measurement by a novel monochrome multiplex quantitative PCR method", Nucleic Acids Research (2009), vol. 37, No. 3, p. e21 (1-7).
Dean, Frank B. et al., "Comprehensive human genome amplification using multiple displacement amplification", PNAS (2002), vol. 99. No. 8, pp. 5261-5266.
Dolezel, J., et al., "Nuclear DNA Content and Genome Size of Trout and Human", Letter to the Editor, Cytometry Part A 51A (2003), pp. 127-128.
Entringer, Sonja et al., "Stress exposure in intrauterine life is associated with shorter telomere length in young adulthood", PNAS (2011), vol. 108, No. 33, pp. E513-E518.
Epel, Elissa S. et al., "Accelerated telomere shortening in response to life stress", PNAS (2004), vol. 101. No. 49, pp. 17312-17315.
Gomes, Nuno M. V., et al., "Comparative biology of mammalian telomeres: hypotheses on ancestral slates and the roles of telomeres in longevity determination", Aging Cell (2011), vol. 10, No. 5, pp. 761-768.

(Continued)

*Primary Examiner* — Kenneth R Horlick
(74) *Attorney, Agent, or Firm* — Troutman Sanders LLP

(57) ABSTRACT

The invention relates to a method for single cell analysis of relative telomere length using multiplex pre-PCR followed by a qPCR (SCT-pqPCR).

34 Claims, 22 Drawing Sheets
Specification includes a Sequence Listing.

(56) References Cited

OTHER PUBLICATIONS

International Preliminary Report on Patentability dated Sep. 15, 2015, which issued during prosecution of International Application No. PCT/US2014/027605, 8 pages.

International Search Report and Written Opinion dated Jul. 21, 2014, which issued during prosecution of International Application No. PCT/US2014/027605, 10 pages.

Kalmbach, Ken Horan, et al., "Telomeres and human reproduction", Fertility and Sterility (2013), vol. 99, No. 1, pp. 23-29.

Keefe, D. L., et. al., "Telomeres and aging-related meiotic dysfunction in women", Cell Mol. Life Sci. (2007), vol. 64, pp. 139-143.

Keefe, David L., et al., "Telomere length predicts embryo fragmentation after in vitro fertilization in women—Toward a telomere theory of reproductive aging in women", American Journal of Obstetrics and Gynecology (2005), vol. 192, pp. 1256-1261.

Kimura, Masayuki et al., "Measurement of telomere length by the Southern blot analysis of terminal restriction fragment lengths", Nature Protocols (2010), vol. 5, No. 9, pp. 1596-1607.

Lansdorp, Peter M., et al., "Heterogeneity in telomere length of human chromosomes", Human Molecular Genetics (1996), vol. 5, No. 5, pp. 685-691.

Lee, Han-Woong et al., "Essential role of mouse telomerase in highly proliferative organs", Nature (1998), vol. 392, pp. 569-574.

Liu, Lin at al., "Telomere lengthening early in development", Nature Cell Biology (2007), vol. 9, No. 12, pp. 1436-1441 and Supplementary Information pp. 1-5.

Ma, Hongxia et al., "Shortened Telomere Length Is Associated with Increased Risk of Cancer: A Meta-Analysis". PLoS One (2011), vol. 6, Issue 6, p. e20466.

Marion, Rosa M. et al., "Telomeres and Telomerase in Adult Stern Cells and Pluripotent Embryonic Stem Cells", The Cell Biology of Stem Celts (2010), Chapter 9, pp. 118-131.

Mosch, B., et al. "Aneuploidy and DNA Replication in the Normal Human Brain and Alzheimer's Disease", The Journal of Neuroscience (2007), vol. 27(26), pp. 6859-6867.

Pan, Xinghua et. al., "A procedure for highly spectfic, sensitive, and unbiased whole-genome amplification", PNAS (2008), vol. 105, No. 40, pp. 15499-15504.

Poon, Steven S. S., et al., "Telomere Length Measurements Using Digital Fluorescence Microscopy", Original Articles, Cytometry (1999), vol. 36, pp. 267-278.

Wang, Fang et al., "Molecular insights into the heterogeneity of tefomere reprogramming in induced pluripotent stem cells", Cell Research (2012), vol. 22, pp. 757-768.

Wright, Woodring E., et al., "Cellular senescence as a tumor-protection mechanism: the essential rote of counting", Current Opinion in Genetics & Development (2001), vol. 11, pp. 98-103.

Zanet, DeAnna L. et al., "Blood and Dried Blood Spot Telomere Length Measurement by qPCR: Assay Considerations", PLoS One (2013), vol. 8, Issue 2, p. e57787.

Zijlmans, J. Mark J. M., el. al., "Telomeres in the mouse have large inter-chromosomal variations in the number of T2AG3 repeats", Proc. Natl. Acad. Sci. USA (1997), Genetics, vol. 94, pp. 7423-7428.

Human

Mouse

METHOD FOR SINGLE CELL ANALYSIS OF TELOMERE LENGTH USING PRE-AMPLIFICATION AND MULTIPLE-COPY REFERENCE SEQUENCE

CROSS-REFERENCE TO RELATED APPLICATIONS

This application is the U.S. National Phase of International Patent Application Serial No. PCT/US2014/027605, filed Mar. 14, 2014, which claims priority to U.S. Provisional Application Ser. No. 61/794,729, filed Mar. 15, 2013, both of which applications are herein incorporated by reference in their entirety.

STATEMENT REGARDING FEDERALLY SPONSORED RESEARCH OR DEVELOPMENT

This invention was made with government support under grants Nos. RR029893, GM099130, and CB941000 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 13, 2014, is named seq243735-121 ST25.txt, and is 2,768 bytes in size.

FIELD OF THE INVENTION

The present invention provides a novel method for single cell analysis of relative telomere length using multiplex pre-PCR followed by a qPCR (SCT-pqPCR).

BACKGROUND OF THE INVENTION

Telomeres are regions of repetitive sequence located at the ends of DNA strands that inhibit deterioration of the vulnerable DNA ends and prevent fusion with neighboring DNA. They provide a buffer to the vital genes located near the ends of chromosomes as DNA at these ends are consumed with rounds of cellular division. In almost all species that have cells with linear chromosomes, telomeres consist of G-rich repeats and associated proteins. In human cells, telomeres are comprised of between less than 0.5 kb to more than 20 kb of (TTAGGG)n repeats which are in dynamic equilibrium with a specific set of proteins. The length of telomeres is heterogeneous but telomeres are present consistently at the end of each chromosome (Moyzis, R et al. (1988) *Proc Natl Acad Sci.* 85: 6622-6626).

The shortening of telomeres over time causes cells to reach a limit in their replication and eventually progress to senescence (Blackburn, E. (2000) *Nature* 408(6808):53-56). Telomere shortening protects against tumorigenesis by limiting cell growth (3, 4), but also can impair tissue regenerative capability and cell viability (5, 6). Shortening of the telomeres can also lead to the activation of a DNA damage response and DNA repair pathways. In some instances, cells are immortalized via telomere lengthening or the activation of telomerase, a telomere lengthening enzyme (Eisenberg, D. (2011). American *Journal of Human Biology* 23 (2): 149-167; Chang, S et al. (2003) *Genes Dev;* 17:88-100). This Alternative Lengthening of Telomeres (ALT) results in genomic instability and leads to disorders, including cancer and age-related diseases. This gradual loss of telomere repeats contributes to replicative senescence or apoptosis in human cells was confirmed and loss of telomeres has been implicated in genomic instability and neoplastic transformation as well as many age-related diseases including aplastic anemia, pulmonary fibrosis or cancer (Murnane et al. (1994). *EMBO J.* 13: 4953-4962.). Hence, the understanding of these complex disorders relies on the study of telomeres and the ability to measure the lengths of telomeric repeats in cells.

The realization that the length of telomere repeats at individual chromosome ends is a critical variable in cell fate decisions and biological functions ranging from aging to carcinogenesis has highlighted the need for techniques that can provide accurate information on the length of telomeres in different cell types.

A number of techniques currently exist in the art which aim to measure telomere length. Reviewed, e.g., in Aubert et al. (2012) *Mutat. Res.* 730:59-67. Thus far, most assays of telomere length measure average telomere length from aggregates of many cells derived from dissected tissues, cultured cells or blood (7).

Terminal Restriction Fragment (TRF) (8) utilizes Southern blot analysis to measure the telomere length of a population of cells to determine the average telomere length of the population. Restriction enzymes which specifically exclude telomere repeats are employed to digest genomic DNA to yield short genomic fragments and longer uncut telomeres. The telomere fragments are separated by agarose gel electrophoresis and detected through either Southern blotting or a hybridization technique which uses a labeled probe to detect telomeric DNA (Kimura, M. (2010) *Natl Protoc.* 5: 1596-1607). This is used to estimate average genomic telomere length by comparison to a DNA ladder size standard and normalization to a reference sample. Attaining sufficient results using TRF requires large amounts of DNA (0.5-5 μg) and several days for processing. Moreover, the requirements for gel electrophoresis and hybridization limit the scalability of this assay. Further, TRF data cannot be readily comparable across studies because techniques are not standardized with respect to restriction enzyme selection, starting DNA quantity and quality, and blot analysis. The technique is also not sensitive enough for short telomeric length measurements.

Single TElomere Length Analysis (STELA) involves the application of single molecule PCR to generate telomere measurements from limited starting material (20 cells or more). The method involves annealing a linker to the telomere overhang and subsequently introducing a linker-specific primer and a primer specific for a unique subtelomeric sequence in a small-pool PCR reaction to generate an individual amplicon for each single telomere (Britt-Compton, B. (2006) *Hum Mol Genet.* 15: 725-733). The biggest drawback of STELA is its requirement for suitable sequences at the ends of the chromosome, and hence, it is only appropriate for several well-characterized ends.

QPCR and related method of MMQPCR (monochrome multiplex QPCR) amplify C- and G-rich strands of the telomere using primers with mismatches present to avoid primer dimer formation and to ensure amplification of solely the telomeric region. This amplification is quantitated and correlated to that of a single copy gene (Cawthon, R. (2002) *Nucleic Acids Res.* 30:e47; Cawthon, R. (2009) *Nucleic Acids Res.* 37:e21; U.S. Patent Appl. Publ. No. 2011/0294676). While the DNA requirement (35 ng or more) for QPCR is significantly less than TRF, it still relies on populations of cells to derive sufficient amounts of DNA.

Quantitative fluorescence in-situ hybridization (QFISH) allows sensitive visualization of relative telomere length from individual cells and individual telomeres, but this method requires many cells and/or metaphase arrested cells, which precludes its application to many sample types, including post-mitotic cells, senescent cells and other non-dividing cells, and when only one actual cell is required to test. In addition, preparing chromosome spreads requires significant technical skill, and only proliferating cells within a population reach metaphase stage, so this analysis potentially biases the estimates of telomere length for a given cell population (10-12). High-throughput quantitative FISH (HT QFISH), Flow FISH and STELA can be used for telomere measurement of dividing, non-dividing and senescent cells, but these methods also require large cell populations (13-15).

Each of the above assays, in addition to their individual drawbacks, cannot be effectively utilized to measure telomere length in single cells in high-throughput format.

SUMMARY OF THE INVENTION

As follows from the Background Section, there is a clear need in the art to develop novel methods for accurately measuring telomere length in samples containing small amounts of DNA, including individual cells. The present invention addresses this and other needs by providing a method for determination of relative telomere length in individual cells using multiplex pre-PCR followed by a qPCR (SCT-pqPCR), which method is characterized by high resolution and scalability.

The ability of the method of the present invention to measure telomere length in single cells rather than relying upon average telomere length in cell populations or the entire tissue enables the study of biological heterogeneity on a cell-by-cell basis, an issue of fundamental importance for assisted reproductive technologies, disease diagnosis and therapy monitoring as well as studies of aging, development, carcinogenesis, and many other processes.

In one embodiment, the present invention provides a method for determining relative telomere length in a biological sample, which sample comprises less than 20 ng of genomic DNA, said method comprising:
 (a) performing a multiplex pre-amplification of DNA contained in the sample for 12-20 cycles using, in a single reaction mixture, a first primer pair specific for a telomere sequence and a second primer pair specific for a reference sequence, wherein the reference sequence is present in multiple copies in the genome,
 (b) performing a qPCR reaction on the products of step (a) using the first and the second primer pairs, wherein such primer pairs are the same as in step (a) and are present in a single or separate qPCR reaction mixtures,
 (c) calculating the T/R ratio as the ratio of (i) the amount of qPCR product obtained in step (b) using the first primer pair specific for the telomere sequence (T) and (ii) the amount of qPCR product obtained in step (b) using the second primer pair specific for the reference sequence (R), and
 (d) determining the relative telomere length for the sample based on the T/R ratio calculated in step (c), wherein the T/R ratio of more than a standard T/R ratio indicates the relative telomere length greater than normal and the T/R ratio of less than the standard T/R ratio indicates the relative telomere length shorter than normal, wherein the standard T/R ratio is (i) a predetermined value, or (ii) an average T/R ratio for multiple corresponding normal cells, tissues or individuals of the same species, or (iii) a standard curve of T/R ratios for multiple corresponding normal cells, tissues or individuals of the same species.

In one specific embodiment, the sample comprises less than 10 pg of genomic DNA. In another specific embodiment, the sample is a single cell (e.g., a polar body, an oocyte, a blastomere, a stem cell [e.g., an embryonic stem cell], a cancer cell, or a fibroblast).

In one specific embodiment, the biological sample is collected from a human subject.

In one specific embodiment, the reference sequence is present in more than 1000 copies per genome. Non-limiting examples of the reference sequences useful in the method of the invention include, e.g., microsatellite sequences and long interspersed repeats (e.g., Alu repeat, B1 repeat, L1 repeat).

In one specific embodiment, prior to step (b) of the method, the pre-amplification products of step (a) are purified.

In one specific embodiment, prior to step (a), the sample is treated with lysis buffer (final concentration: 100 mM Tris-HCl pH 7.4, 300 mM NaCl, 0.8 mM EDTA, 2% NP-40 and 5 mM DTT).

In one specific embodiment, DNA Polymerase Hot Start Version is used for step (a).

In one specific embodiment, the first primer pair specific for the telomere sequence is Tel-F (CGGTTT-GTTTGGGTTTGGGTTTGGGTTTGGGTTTGGGTT, SEQ ID NO: 1) and Tel-R (GGCTTGCCTTACCCTTAC-CCTTACCCTTACCCTTACCCT, SEQ ID NO: 2).

In one specific embodiment, the reference sequence is Alu repeat and the second primer pair specific for the reference sequence is hAlu-F (GACCATCCCGGCTAAAACG, SEQ ID NO: 3) and hAlu-R (CGGGTTCACGCCATTCTC, SEQ ID NO: 4).

In one specific embodiment, the pre-amplification step (a) is performed using the following sequence of cycles:
 (i) melting at 94° C. for 5 minutes, followed by
 (ii) 16-18 cycles: melting at 94° C. for 15 seconds, annealing at 60° C. for 30 seconds, and extension at 72° C. for 30 seconds, followed by
 (iii) final extension for 10 minutes at 72° C.

In one specific embodiment, the qPCR step (b) is performed using the following sequence of cycles:
 (i) melting at 95° C. for 10 minutes, followed by
 (ii) 40 cycles: melting at 95° C. for 15 seconds, annealing at 60° C. for 30 seconds, and extension at 72° C. for 30 seconds, followed by
 (iii) 80 cycles of melting curve from 60° C. to 95° C.

In one specific embodiment, the T/R ratio is determined for two or more different reference sequences simultaneously.

In one specific embodiment, the amount of qPCR product is determined using a fluorescent label.

In one specific embodiment, the pre-amplification in step (a) is performed for 16-18 cycles. If the sample is human, the pre-amplification in step (a) is preferably performed for 17 cycles. If the sample is murine, the pre-amplification in step (a) is preferably performed for 16 cycles.

In one specific embodiment, the standard T/R ratio is 1.

In conjunction with the above method for determining relative telomere length, the present invention also provides a method for identifying the presence of a disease involving telomere abnormalities (e.g., cancer, bone marrow failure, pulmonary fibrosis, infertility related to egg dysfunction, precocious aging, and genetic conditions which disrupt normal telomere elongation, etc.) in a biological sample (e.g., a single cell or a number of cells), said method comprising:
(a) determining relative telomere length in the biological sample using the method for determining relative telomere length (as described above), and
(b) identifying the presence of a disease involving telomere abnormalities if the T/R ratio in the biological sample differs from the standard T/R ratio.

In a separate embodiment, the invention provides a method for predicting viability of an oocyte (e.g., in connection with assisted reproductive technologies), said method comprising:
(a) determining relative telomere length in a polar body corresponding to the oocyte using the method for determining relative telomere length (as described above), and
   (b) (i) determining that the oocyte has high viability if the T/R ratio in the polar body is similar to the standard T/R ratio, or (ii) determining that the oocyte has low viability if the T/R ratio in the polar body differs from the standard T/R ratio, wherein the standard T/R ratio is an average T/R ratio or a standard curve of T/R ratios for multiple healthy oocytes from healthy oocyte donors.

In a further embodiment, the invention provides a method for predicting chromosomal stability of an oocyte (e.g., in connection with assisted reproductive technologies), said method comprising:
(a) determining relative telomere length in a polar body corresponding to the oocyte using the method for determining relative telomere length (as described above), and
(b) (i) determining that the oocyte has high chromosomal stability if the T/R ratio in the polar body is similar to the standard T/R ratio, or (ii) determining that the oocyte has chromosomal instability if the T/R ratio in the polar body differs from the standard T/R ratio, wherein the standard T/R ratio is an average T/R ratio or a standard curve of T/R ratios for multiple healthy oocytes from healthy oocyte donors.

In another embodiment, the invention provides a method for predicting viability of an embryo (e.g., in connection with assisted reproductive technologies), said method comprising:
(a) determining relative telomere length in one or more blastomeres isolated from the embryo using the method for determining relative telomere length (as described above), and
(b) (i) determining that the embryo has high viability if the T/R ratio in the one or more blastomeres is similar to the standard T/R ratio, or (ii) determining that the embryo has low viability if the T/R ratio in the one or more blastomeres differs from the standard T/R ratio, wherein the standard T/R ratio is an average T/R ratio or a standard curve of T/R ratios of one or more blastomeres from an embryo that created the pregnancy.

In yet another embodiment, the invention provides a method for predicting chromosomal stability of an embryo (e.g., in connection with assisted reproductive technologies), said method comprising:
(a) determining relative telomere length in one or more blastomeres isolated from the embryo using the method for determining relative telomere length (as described above), and
(b) (i) determining that the embryo has high chromosomal stability if the T/R ratio in the one or more blastomeres is similar to the standard T/R ratio, or (ii) determining that the embryo has chromosomal instability if the T/R ratio in the one or more blastomeres differs from the standard T/R ratio, wherein the standard T/R ratio is an average T/R ratio or a standard curve of T/R ratios of one or more blastomeres from an embryo that created the pregnancy.

BRIEF DESCRIPTION OF THE DRAWINGS

FIG. 1A is a schematic diagram of the two tier SCT-pqPCR protocol. Outer lighter dots and inner darker dots represent telomere sequence and reference gene sequence in chromosome, respectively. The thick and thin lines represent telomere primer and reference gene primer respectively. The thick and thin lines represent PCR productions by Tel and Alu primers, respectively, after pre-amplification. FIG. 1B is a melt peak of primers for telomeres (Tel) and references genes Alu, 18srDNA, and 36B4 by qPCR after pre-amplification of DNA from a single human HelaS3 cell. FIG. 1C is a melt peak of primers for telomeres (Tel) and references genes B1, 18srDNA, and 36B4 by qPCR after pre-amplification of DNA from a single mouse tail tip fibroblast (TTF) cell. FIG. 1D is a line graph of the linear correlation analysis of relative telomere length of a population of cells by regular qPCR between single copy gene and multi-copy genes as reference genes. FIG. 1E is a line graph of the linear correlation analysis of telomere length of a population of cells by telomere restriction fragment (TRF) and regular qPCR using multi-copy genes as reference genes. FIG. 1F is a bar graph of the mean Ct value resulting from pre-amplification by Tel and Alu primers using different concentrations of human fibroblast DNA samples at varying pre-PCR cycle numbers (1-16). FIG. 1G is a bar graph of the mean Ct value resulting from pre-amplification by Tel and Alu primers using different concentrations of human fibroblast DNA samples at varying pre-PCR cycle numbers (12-20).

FIG. 2A shows a series of bar graphs presenting the relative telomere length measurement (T/R ratio) determined by regular qPCR when normalized to a single copy gene 36B4 (top panel) and multi-copy reference genes (Alu and 18srDNA; middle and bottom panels, respectively). FIG. 2B is a Southern blot analysis of telomere restriction fragment (TRF) determination for various human primary cells, cell lines and embryonic cells. Lane M is the DNA marker.

FIG. 3A shows the amplification curves determined by qPCR of genomic DNA using different primers (Tel and Alu, left panel; Tel and B1, right panel) and different starting concentrations of genomic DNA ranging from DNA from 1 cell to 10 ng in human (left panel) and mouse (right panel) cells. FIG. 3B shows the standard curves determined to use for the calculation of relative telomere length as T/R ratio. The left curve was generated from human cell DNA and the right curve was generated from mouse cell DNA.

FIG. 4A is a bar graph of the T/R ratio obtained from SCT-pqPCR for primary human cells using a 17-cycle pre-PCR. FIG. 4B is a bar graph of the T/R ratio obtained from SCT-pqPCR for human cell lines using a 17-cycle pre-PCR. FIG. 4C is a bar graph of the QFISH analysis on metaphase chromosomes for primary human cells. FIG. 4D is a bar graph of the QFISH analysis on metaphase chromosomes for human cell lines. For each of FIGS. 4A-D, shown in parentheses is the "mean±s.d., coefficient of variation (CV)".

FIG. 5A is a line graph showing that the average relative telomere length in single cells determined by SCT-pqPCR correlates with that of a cell population shown as the T/S ratio by regular qPCR. The Pearson test was applied. FIG. 5B is a line graph showing that the average telomere length in single cells (T/R ratio) determined by SCT-pqPCR correlates with quantitative telomere length as determined by QFISH. FIG. 5C is a line graph showing that the average telomere length in single human cells determined by SCT-pqPCR correlates with the absolute telomere length of population cells determined by TRF. FIG. 5D is a line graph showing that the quantitative telomere length of metaphase cells determined by QFISH correlates with the absolute telomere length of cell populations determined by TRF. Open-square dots represent HelaS3 cancer cell, closed-square dots represent human lung fibroblast from a 71-year old donor (F200), open-circle dots represent human lung fibroblast from a 14-week gestation (F171), closed-circle dots represent SaOS2 ALT cell, closed-triangle dots represent human embryonic stem cell (RuES2) and open-triangle dots represent U2OS ALT cell.

FIG. 7A shows a series of bar graphs of the T/R ratio of single cell telomere length relative to the reference gene B1 by SCT-pqPCR (top panel) and QFISH (bottom panel) in mouse cells (TTF and mES). FIG. 7B shows a series of bar graphs of the T/R ratio of single cell telomere length relative to the reference gene Alu by SCT-pqPCR (top panel) and QFISH (bottom panel) in human cell lines (HelaS3 and 1301). FIG. 7C is bar graphs depicting the average telomere length of single cells as compared to the average telomere length of cell populations in mouse. FIG. 7D is bar graphs depicting the average telomere length of single cells as compared to the average telomere length of cell populations in human cells. For both FIGS. 7C and 7D, the left graph is the average telomere length of single cells as a mean of T/R ratio by SCT-pqPCR and the right graph is the average telomere length of cell populations as T/S ratio by regular qPCR. FIG. 7E depicts the telomere length distribution in metaphase chromosomes of mouse cell populations by QFISH. FIG. 7F depicts the telomere length distribution in metaphase chromosomes of human cell populations by QFISH. For both FIGS. 7E and F, the average telomere length as telomere fluorescence unit (TFU) is indicated as Mean±Sd.

FIG. 8A is a bar graph of the T/R ratio of the measurement of single cell telomere length by SCT-pqPCR between 2 sister cells from a mouse 2-cell (2c) embryo. FIG. 8B shows the telomere length correlation between 2 sister cells of a 2-cell embryo. FIG. 8C is a bar graph of the T/R ratio of the measurement of single cell telomere length by SCT-pqPCR between human oocytes (0) and their polar bodies. FIG. 8D shows the telomere length correlation between a human oocyte and its paired polar body. FIG. 8E is a bar graph of the T/R ratio of the measurement of single cell telomere length by SCT-pqPCR between 2 sister cells from the cultured human cell line HeLaS3 (H). FIG. 8F shows the telomere length correlation of two daughter cells for the 10 pairs of cells of HelaS3 cells assayed by SCT-pqPCR.

FIG. 10A is the frequency distribution of telomere fluorescence in metaphase chromosomes of three different human lung fibroblasts cells as determined by QFISH. The average telomere length of telomere fluorescence unit (TFU) is indicated. FIG. 10B is a bar graph of the relative telomere length (ratio T/S) related to 36B4 expressed by qPCR in these three human lung fibroblast cells.

FIG. 11A is a bar graph that summarizes the telomere length (T/R ratio) for multiple individual cells as measured by SCT-pqPCR. FIG. 11B is a bar graph that summarizes the telomere length (T/R ratio) for multiple individual cells as measured by QFISH. O represents outliers; * represents extreme value (i.e., value outside the range of measurement of the assay—here value outside the 3 box length range from the upper and lower value of the box). FIG. 11C is a bar graph of telomere lengthening of single cells over time as shown for mouse zygotes, 2C and 4-cell (4C) embryos. FIG. 11D is a bar graph of average telomere length in different stage mouse embryos as analyzed by the Student Newman-Keuls test.

DETAILED DESCRIPTION OF THE INVENTION

Figure 1A:
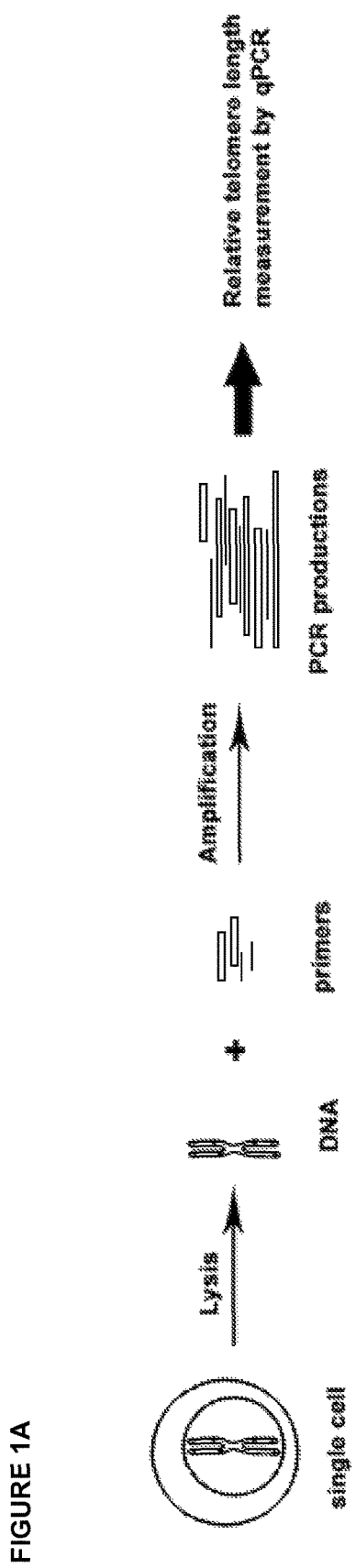
FIGS. 1A-G describe the design of SCT-pqPCR.

The present invention provides a simple and robust approach for single cell telomere length measurement based on multiplex pre-PCR followed by a qPCR (SCT-pqPCR). The basis of the present assay is that within a given cell, the ratio of the copy number of telomere repeats (T) to the copy number of a multi-copy reference gene (R) is fixed. The present inventors have adapted qPCR to measure telomere length in individual cells by employing a pre-amplification step that specifically targets both the telomere and one or more multi-copy reference genes, followed by a qPCR assay to obtain T/R ratio(s). The use of multi-copy genes (preferably genes with more than 1000 copies per genome) as reference genes (as compared to existing QPCR methods using single copy reference genes) helps avoid amplification bias from single cells since each multi-copy gene targets an abundant sequence, similar to the abundant telomere units, within the single cells. Another unique aspect of the assay of the invention is the single-tube pre-amplification of the reference gene in parallel with the telomere sequences for a limited number of cycles by multiplex pre-PCR, which avoids sample loss, and retains a faithful ratio of products, yet significantly expands material for measurements by qPCR.

The pre-PCR step of the method of the invention uses a limited number of cycles (12-20) to retain the original ratio of the telomere (T) to the reference sequence (R), using multiple sets of PCR primers (i.e., two or more different primer pairs) to generate sufficient amounts of amplification product to enable further amplification in the 2nd step (qPCR). The multiple aliquots are preferably used for qPCR for statistical analysis of reliability and bias. The method of the invention also preferably includes a single tube extraction of DNA (e.g., using lysis buffer which contains 100 mM Tris-HCl pH 7.4, 300 mM NaCl, 0.8 mM EDTA, 2% NP-40, and 5 mM DTT (final concentration)) directly from single cells (or low quantity cells) for pre-PCR, to avoid loss of genomic DNA.

As described in the Examples section, below, the present inventors have optimized a multiplex pre-amplification specific for telomeres and reference genes from individual cells, such that the amplicon provides a consistent ratio (T/R) of telomeres (T) to the reference genes (R) by qPCR. The average T/R ratio of multiple single cells measured by the method of the present invention corresponded closely to that of a given cell population measured by regular qPCR, and correlated with those of telomere restriction fragments (TRF) and Q-FISH measurements. Furthermore, SCT-pqPCR detected the telomere length for quiescent cells that are inaccessible by Q-FISH. The reliability of telomere length measurement by SCT-pqPCR also was confirmed using sister cells from two cell embryos. The heterogeneity of telomere length among several populations of cells by SCT-pqPCR run on multiple single cells is consistent with, and sometimes superior to, results obtained by Q-FISH. Telomere length heterogeneity was then identified by SCT-pqPCR among cells of various human and mouse cell types. It was found that the T/R values of human fibroblasts at later passages and from old donors were lower and more heterogeneous than those of early passages and from young donors, that cancer cell lines show heterogeneous telomere lengths, that human oocytes and polar bodies have nearly identical telomere lengths, and that the telomere lengths progressively increase from the zygote, 2-cell to 4-cell embryo. Based on these and other results described herein, it follows that the method of the invention provides the ability to determine telomere length in individual cells and facilitates understanding of telomere heterogeneity and its role in tumorigenesis, development, aging and associated diseases.

In one embodiment, the present invention provides a method for determining relative telomere length in a biological sample (including a single intact cell) isolated from any species with chromosome telomeres, which sample comprises less than 35 ng of genomic DNA, preferably less than 20 ng of genomic DNA, and more preferably less than 10 pg of genomic DNA, said method comprising:
(a) performing a multiplex pre-amplification of DNA contained in the sample for 12-20 cycles (preferably, 16 cycles for mouse samples and 17 cycles for human samples) using, in a single reaction mixture, a first primer pair specific for a telomere sequence and a second primer pair specific for a reference sequence, wherein the reference sequence is present in multiple copies in the genome,
(b) performing a qPCR reaction on the products of step (a) using the first and the second primer pairs, wherein such primer pairs are the same as in step (a) and are present in a single or separate qPCR reaction mixtures,
(c) calculating the T/R ratio as the ratio of (i) the amount of qPCR product obtained in step (b) using the first primer pair specific for the telomere sequence (T) and (ii) the amount of qPCR product obtained in step (b) using the second primer pair specific for the reference sequence (R), and
(d) determining the relative telomere length for the sample based on the T/R ratio calculated in step (c), wherein the T/R ratio of more than a standard T/R ratio indicates the relative telomere length greater than normal and the T/R ratio of less than the standard T/R ratio indicates the relative telomere length shorter than normal, wherein the standard T/R ratio is (i) a predetermined value, or (ii) an average T/R ratio for multiple corresponding normal cells, tissues or individuals of the same species, or (iii) a standard curve of T/R ratios for multiple corresponding normal cells, tissues or individuals of the same species.

As used herein in connection with pre-amplification step (a), the term "multiplex pre-amplification" or "multiplex PCR" refers to a DNA amplification reaction which is performed using two or three pairs of primers in the same reaction. Such multiplex pre-amplification/PCR is distinguishable from a regular PCR which employs one pair of primers (forward and reverse). Non-limiting examples of primers useful for multiplex pre-amplification step (a) in the method of the present invention are as follows:

| Primer | Sequence | SEQ ID NO |
|---|---|---|
| Tel-F | CGGTTTGTTTGGGTTTGGGTTTGGGTTTGGGTTTGGGTT | 1 |
| Tel-R | GGCTTGCCTTACCCTTACCCTTACCCTTACCCTTACCCT | 2 |
| hAlu-F | GACCATCCCGGCTAAAACG | 3 |
| hAlu-R | CGGGTTCACGCCATTCTC | 4 |
| mB1-F | GCACCTTTAATCCCAGCAC | 5 |
| mB1-R | TGAGACAGGGTTTCTCTGTA | 6 |

*m represents mouse; h represents human

Because the telomere DNA sequence is $(TTAGGG)_n$ hexamer repeats, each telomere-specific primer used in the method of the invention is designed to allow DNA polymerase to extend from its 3'-end when it is hybridized to telomere hexamer repeats but not when it is hybridized to the other primer. The last six bases on the 5'-end of each primer cannot base pair with the telomere sequence when the rest of the primer is optimally hybridized. The complements of these 5'-sequences are generated at the 3'-ends of all products that are completed in each cycle of the PCR, thereby blocking those 3'-ends from initiating DNA synthesis in the middle of telomere amplification products in subsequent cycles. Telomere specific primers are both able to primer at multiple locations along the tandem repeats of telomeric DNA, therefore they generate a series of products of various length. The resulting telomere PCR signal (e.g., measured as the level of SYBR Green fluorescence) is a measure of telomere length, because the number of telomere primers that can bind the telomeric DNA at the beginning of the PCR is directly proportional to the total summed length of all the telomeres in the cell. In one specific embodiment, the telomere-specific primer pair used in the method of the invention is Tel-F (CGGTTT-GTTTGGGTTTGGGTTTGGGTTTGGGTTTGGGTT, SEQ ID NO: 1) and Tel-R (GGCTTGCCTTACCCTTAC-CCTTACCCTTACCCTTACCCT, SEQ ID NO: 2).

In contrast to the method of the present invention, the forward primer used for MMQ-PCR method of telomere length determination is able to prime DNA synthesis along native telomeric DNA sequences (Zanet et al., PLoS One. 2013, 8(2):e57787). The reverse primer used for MMQ-PCR is blocked from priming native telomeric DNA by a mismatched base at its 3' terminus. However, the reverse primer is able to hybridize along various stretches of the forward primer extension product, and exactly one configuration of those hybridizations allows the priming of DNA synthesis, thereby enabling the generation of a single, fixed-length product.

The primers used for STELA method of telomere length determination are very different from the telomere-specific primers of the method of the present invention (Barid et al., Nature Genetics, 2003, 33(2):203-207; Aubert et al., Mutat Res., 2012, 730(1-2):59-67). The forward primer is a chromosome-specific and located in the subtelomeric region. The reverse primer is complementary with the telorette tail that is ligated to the 5' end of the complementary C-rich strand of the chromosome. The product is full length of telomere DNA of specific chromosome.

The reference sequence useful in the method of the present invention is a sequence which is present in multiple copies in the genome, preferably in more than 1000 copies per genome. Non-limiting examples of useful reference sequences include, e.g., interspersed repeats and microsatellite sequences (such as, e.g., Alu repeat, B1 repeat and L1 repeat). In one specific embodiment, the reference sequence is Alu repeat, which is about 300 base pairs long and is one of the most abundant interspersed repeats in the genome (total copy number of about 1 million). Because the telomere sequence contains GGG and Alu repeats contain GC, the melting temperature (Tm) for PCR is high (60° C.). In one specific embodiment, the human Alu-specific reference primer pair used in the method of the invention is hAlu-F (GACCATCCCGGCTAAAACG, SEQ ID NO: 3) and hAlu-R (CGGGTTCACGCCATTCTC, SEQ ID NO: 4).

In one specific embodiment, the multiplex pre-amplification step (a) of the method of the invention is conducted as follows:

The reaction system in a PCR tube consists of the following:

| | |
|---|---|
| Single cell genomic DNA | 2 μl |
| 10 × PCR buffer | 4 μl |
| 2.5 mM dNTP | 4 μl |
| DNA polymerase | 0.25 μl |
| Telomere forward primer (10 μM) | 1 μl |
| Telomere reverse primer (10 μM) | 1 μl |
| Multi-copy gene forward primer (10 μM) | 1 μl |
| Multi-copy gene reverse primer (10 μM) | 1 μl |
| Water | 5.75 μl |
| Total volume | 20 μl |

Thermal Cycler Reaction Conditions:
(i) melting at 94° C. for 5 minutes, followed by
(ii) 16-18 cycles (preferably, 16 cycles for a mouse sample and 17 cycles for a human sample): melting at 94° C. for 15 seconds, followed by annealing at 60° C. for 30 seconds and extension at 72° C. for 30 seconds, followed by
(iii) final extension for 10 minutes at 72° C.

In one specific embodiment, the qPCR step (b) of the method of the invention is performed using the following sequence of cycles:
(i) melting at 95° C. for 10 minutes, followed by
(ii) 40 cycles: melting at 95° C. for 15 seconds, annealing at 60° C. for 30 seconds, and extension at 72° C. for 30 seconds, followed by
(iii) 80 cycles of melting curve from 60° C. to 95° C. ("melting curve" should be consistent in the samples tested, i.e., it should have a consistent peak pattern with one major peak, otherwise, there may have been non-specific amplification).

The amount of qPCR product in step (c) of the method of the invention can be determined by any method known in the art, including gel electrophoresis followed by measurement of fluorescence signal using various labels such as, e.g., SYBR green.

The term "standard T/R ratio" as used herein in connection with determining relative telomere length in step (d) of the method of the invention, encompasses predetermined values (e.g., a published value in a reference) as well as average T/R ratios or standard curves of T/R ratios determined experimentally for multiple similarly processed corresponding normal cells, tissues or individuals of the same species (e.g., young healthy subjects for ageing or reproductive telomere analysis, age-matched healthy subjects for cancer-related telomere analysis, etc.). As used herein, the term "similarly processed" refers to samples which have been obtained and treated using the same protocol for purification and amplification.

DNA sample(s) which are used as a standard in the method of the invention may be used to create standard curves (e.g., such curves can be created from five or more different input DNA of the same sample), as long as the Ct of each assayed sample falls within the range of Ct values of the standard curves. The Ct of a DNA sample for each primer pair is the fractional number of PCR cycles to which the sample must be subjected in order to accumulate enough product to cross a set threshold of magnitude of the detection signal (e.g., fluorescence signal obtained using various labels such as, e.g., SYBR green).

As used herein, the term "Ct value" is defined as the "cycle threshold value". It is the number of cycles required for the measured output signal (e.g., fluorescent signal) to cross the threshold, the background level of the assay. Ct levels are inversely proportional to the amount of target.

In one embodiment of the method of the invention, prior to step (b), the pre-amplification products of step (a) are purified. Non-limiting examples of useful purification methods include, for example, filtration (e.g., using Sephadex columns), enzymatic purification (e.g., using ExoSAP-IT or related exonuclease cocktail), sodium acetate and ethanol precipitation, and purification using magnetic beads (e.g., using Agencourt AMPure XP). In order to perform a high throughput analysis of telomere length for multiple (e.g., hundreds) of single cells in parallel, the pre-PCR product is preferably cleaned up either by in-tube digestion of the primers and left-over genomic DNA with enzyme (e.g., using ExoSAP-IT or related exonuclease cocktail) or by a magnetic bead-based purification (e.g., using Agencourt AMPure XP). Such clean-up step can be combined with 96-well or 384-well plates.

The microfluidic system that allows qPCR such as Fluidigm also may be adapted with the SCT-pqPCR method of the invention to achieve high throughput.

The method of the present invention can be used for numerous applications of analysis and study. Such applications include, but are not limited to, analyzing for the presence of shortened telomeres, analyzing for the presence of lengthened telomeres, analyzing the presence of abnormal numbers of telomeres (the latter application would involve measuring the average telomere length of a population of cells).

The method of the present invention can be used for diagnosis of diseases involving telomere abnormalities. Non-limiting examples of such diseases include, for example, cancer, bone marrow failure, pulmonary fibrosis, infertility related to egg dysfunction, precocious aging, and genetic conditions which disrupt normal telomere elongation. The method of the invention can be also used for monitoring of effectiveness of existing therapies and development of new therapies for such diseases. For example, the method of the invention can be used to screen the viability of human stem cells before cancer treatment or to screen chemotherapeutic agents targeted to cancer stem cells, which are quite limited in number.

Single cell telomere estimation using the method of the present invention can be also used to predict the viability and chromosomal stability of oocytes and embryos for women undergoing assisted reproductive technologies (e.g., by measuring telomere length in individual polar bodies or blastomeres to reflect egg quality). Work by the present inventors and co-workers showed that the telomere lengths of the chromosomes in the polar body and in the sister oocyte are highly correlated (r2 98.5%) (see, e.g., Kalmbach et al., Fertil Steril., 2013, 99(1):23-29; Kalmbach et al., Cell Mol Life Sci., 2007, 64(2):139-143; Keefe et al., Am J Obstet Gynecol., 2005, 192(4):1256-1260; discussion 1260-1). Thus, a polar body can be removed and its telomere length can be measured before fertilization of the egg. Another approach could be to use sister eggs ovulated but not fertilized during the in vitro fertilization (IVF) process. Work by the present inventors and co-workers showed that the telomere lengths among sister eggs are highly correlated (see, e.g., Kalmbach et al., Fertil Steril., 2013, 99(1):23-29; Kalmbach et al., Cell Mol Life Sci., 2007, 64(2):139-143; Keefe et al., Am J Obstet Gynecol., 2005, 192(4):1256-1260; discussion 1260-1). Thus, the method of the invention can help women decide whether to continue to pursue treatments which depend on their own eggs, or pursue alternatives, such as egg donation or adoption. In addition, the method of the invention can help select which embryo to transfer and thus reduce the risk of multiple gestation. Another use of the method of the invention would be to help women going through egg retrieval for egg freezing determine whether they have frozen a viable egg (e.g., by using the telomere length in the corresponding polar body to predict viability).

By providing the ability to measure telomere length in individual cells, the method of the present invention also allows the understanding and study of embryonic development, aging as well as numerous disorders related to telomere shortening, including cancers and reproductive disorders. For example, the method of the invention will facilitate the identification and functional studies of cancer stem cells and pluripotent stem cells, and will allow to distinguish them from other cells in a mixed populations (24), and advance the understanding of the molecular mechanisms underlying the variation of individual cells in development, disease, senescence and tumorigenesis (25).

An "individual" or "subject" or "animal", as used herein, refers to humans, veterinary animals (e.g., cats, dogs, cows, horses, sheep, pigs, etc.) and experimental animal models of diseases (e.g., mice, rats, etc.). In a preferred embodiment, the subject is a human.

The term "polar body" used herein refers to the small, non-egg cell, that results when a diploid cell undergoes cytokinesis and uneven division following meiosis.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nuc. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Establishment of Single Cell Quantitative PCR for Telomere Length Measurement (SCT-pqPCR)

Methods

Cell and Embryo Culture:
The cells used were as follows: human cells HelaS3 (FIGS. 1B,D,E and 2A,B), mouse tail tip fibroblasts (FIGS.

Figure 1B:
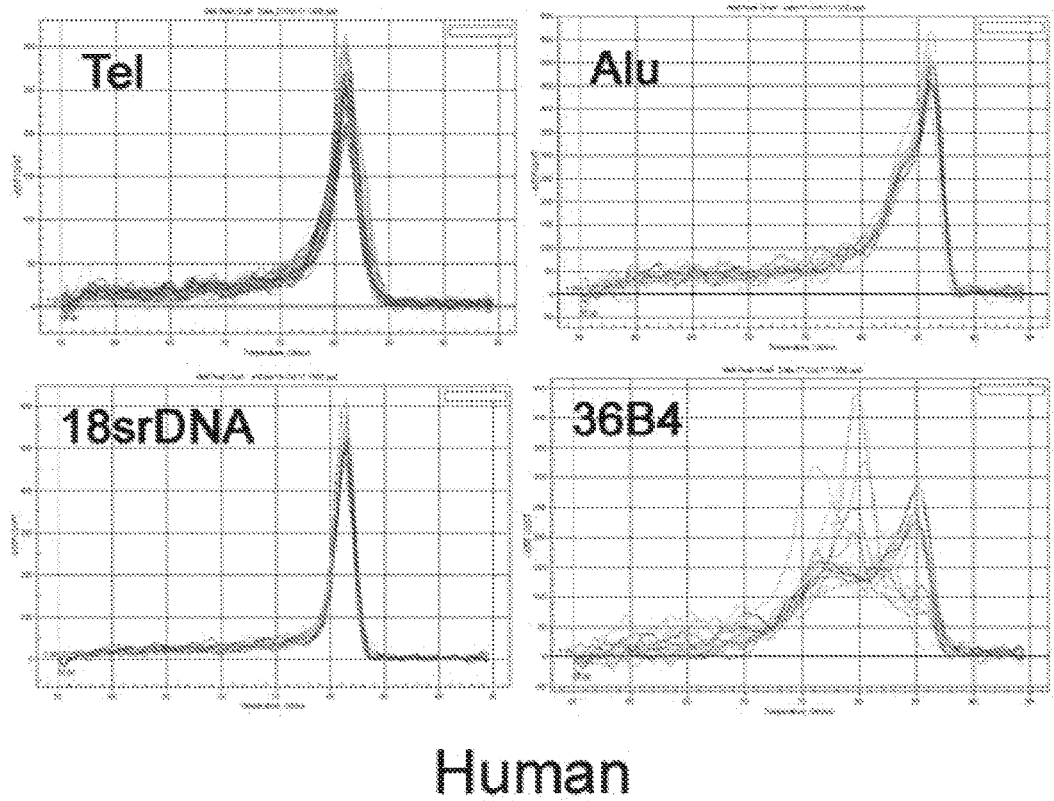
Figure 1C:
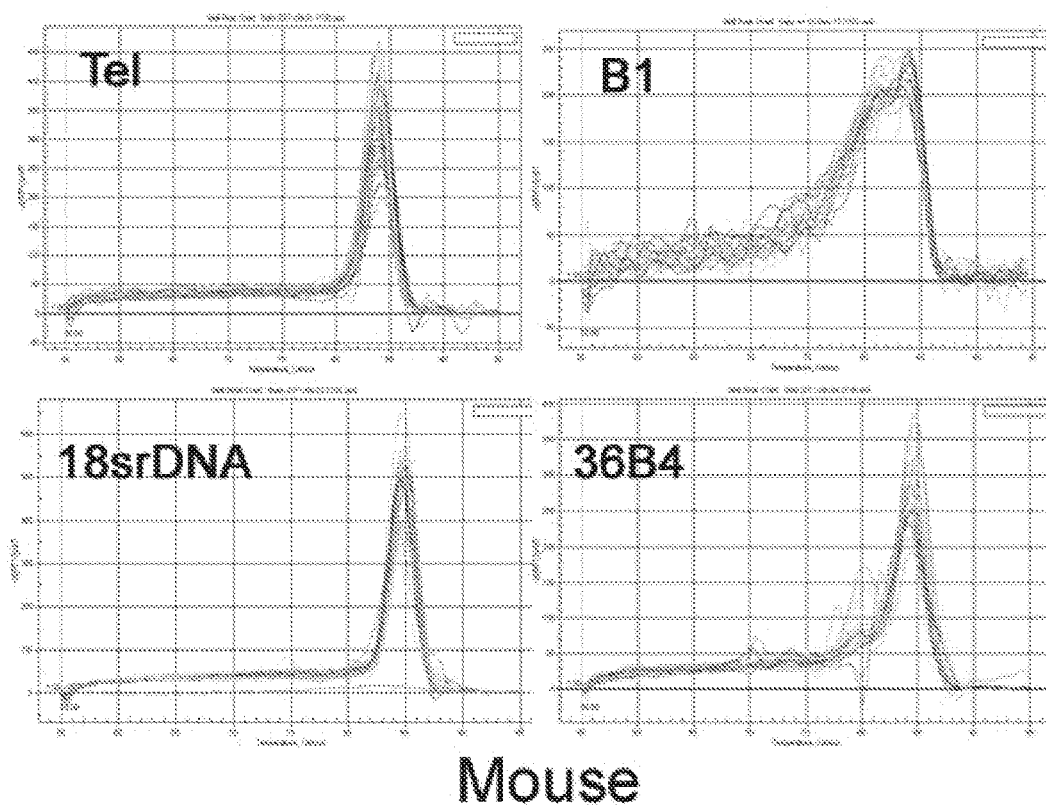
Figure 1D:
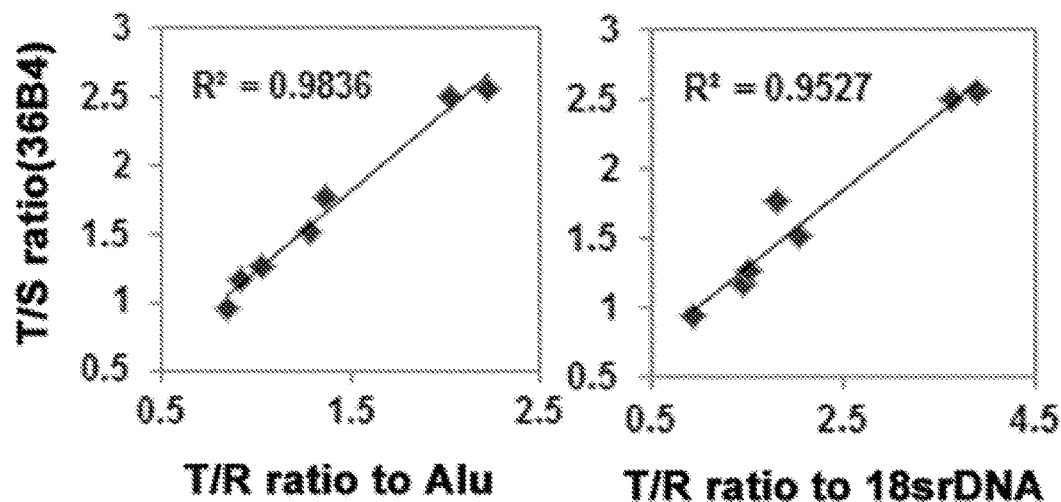

1C and 3B), human cells 1301, Rues2, U2OS, SaOS2 and human lung fibroblasts 200 (FIGS. 1D, E and 2A,B), human lung fibroblasts 171 (FIGS. 1D,E,F,G, 2A,B and 3A). Human lung fibroblasts (ATCC, #CCL-171, #CCL-200 and #CCL-204) were cultured in Eagle's Minimum Essential Medium (EMEM) (ATCC, #30-2003) supplemented with 10% (vol/vol) FBS (Fisher scientific, # SH30070.03E). The HelaS3 cell line (Canela et al., Proc Natl Acad Sci USA, 2007, 104(13):5300-5305) and the 1301 cell line (T-cell leukemia, Sigma, Catalog #01051619) were cultured in RPMI medium 1640 (Invitrogen) supplemented with 10% FBS, 2 mM Glutamine (Invitrogen), 100 U/ml penicillin and 100 µg/ml streptomycin (Invitrogen). Mouse tail tip fibroblasts (TTF) were cultured in DMEM (Invitrogen) supplemented with 10% FBS and 100 U/ml penicillin and 100 µg/ml streptomycin.

Single Cell Isolation and DNA Extraction:

Single cells were isolated and lysed in a PCR tube and genomic DNA was extracted using the Tissue and Blood DNA extraction kit (Qiagen). Single cell genomic DNA was obtained by adding 4µl lysis buffer 2× (100 mM Tris-HCl pH 7.4, 300 mM NaCl, 0.8 mM EDTA, 2% NP-40 and 5 mM DTT) into a single cell with volume less than 1 µl (with buffer), and heated at 75° C. for 5 minutes. Single cell genomic DNAs with lysis buffer were stored at −20° C.

Single Cell Genomic DNA Amplification by Pre-PCR with Primers of Telomere and Reference Gene and the Subsequent Product Purification:

Pre-PCR was performed using DNA Polymerase Hot Start Version (TAKARA). The reactions were set up by aliquoting 38 µl of master mix into the 0.2 µl PCR tubes each with 2 µl single cell genomic DNA. Each reaction was set up with by 4 µl 10×PCR buffer, 4 µl 2.5 mM dNTP, 0.25 µl DNA polymerase, 1 µl each of telomere forward and reverse primer (10 µM), and 1 µl each of multi-copy gene forward and reverse primer (10 µM) or single gene primer 36B4 (10 µM) and up to a 40 µl final volume with water. Thermal cycler reaction conditions were set at 94° C. for 5 minutes followed by different cycles of 94° C. for 15 seconds, 60° C. annealing for 30 seconds and extension at 72° C. for 30 seconds, with a final extension for 10 minutes at 72° C. PCR products were purified following the protocol of a commercially available purification kit, DNA Clean and Concentrator-5 (Zymo research). The purified PCR products were eluted in 64 µl double distilled water.

QPCR Assay for Single Cell Telomere Measurement:

Telomere length of single cells was measured by qPCR after pre-PCR, purification and aliquoting. The reaction was set up with SYBR Green I in 96-wells plates. The purified products of pre-PCR for each single cell were aliquoted with 5 µl into each well of a 96-well plate. Three repeat reactions were performed for each sample plus each pair of primers. The final master mix of each well in the qPCR was 10 µl 2×SYBR Green mix, 0.5 µl each of forward and reverse primer (10 µM for Tel, Alu, B1 and 36B4) and 4 µl molecular-filtered water. The qPCR conditions were the same as above. The results were analyzed by CFX manager software and the relative telomere length of single cells was calculated by the T/R ratio.

Southern Blot Analysis of TRF:

Telomere restriction fragment analysis was performed as described by using the TeloTAGGG Telomere Length Assay Kit (Roche) according to the provided protocol. The mean telomere length was calculated using the equation (26): TRF=Σ(ODO/Σ(ODi/Li), whereby ODi was the chemiluminescent signal and ODi/Li was the length of the TRF at position.

Data Statistics:

All the data statistics were obtained using the SPSS 13.0 software (IBM software SPSS). The P value for comparison of two groups was derived from the independent-samples T test. Statistical data from the multiple groups was analyzed with one-way ANOVA. The frequency of telomere distribution was compared by a non-parametric test. The correlation analysis was performed by the Pearson correlation test. Alpha is set at 0.05 for all tests.

Results

Described herein is a novel strategic approach and analysis developed based on quantitative PCR (qPCR) to analyze relative telomere length in single cells. A comparison of the lengths of telomeres and reference genes was determined using a novel protocol requiring parallel pre-amplification of the target sequences followed by qPCR of these target genes (FIG. 1A). The pre-amplification step, referred to as multiplex PCR or qPCR, was designed to retain the original ratio of telomere length to that of the reference sequences.

A single cell possesses approximately 6-7 picograms of genomic DNA (18), but the original qPCR assay requires nanogram amounts of DNA to measure telomere length (9). To avoid DNA loss from the extremely small sample size of a single cell during physical purification, a lysis buffer containing EDTA and NP-40 was utilized to gently release DNA and retain DNA integrity. Due to the processing requirement for such a sample size, the buffer was prepared so as to remain compatible with the subsequent PCR reaction as below:

| Final 2X buffer | Stock concentration (mM) | Volume of stock (µl) |
|---|---|---|
| 100 mM Tris-HCL pH 7.4 | 1000 | 100 |
| 300 mM NaCl | 5000 | 60 |
| 0.8 mM EDTA | 500 | 1.6 |
| 2% NP-40 | 10 | 200 |
| 5 mM DTT | 1000 | 5 |
| Water | | 633.4 |
| Final volume | | 1000 |

This method determines telomere length from a single DNA cell, hence robust and faithful pre-amplification of the telomere sequence and reference gene/s from single cells, without distortion of their native ratio, is critical for this assay. Various reference genes, including a single copy gene and several multi-copy genes, were tested as candidate normalization references for the telomere units. The single copy gene 36B4 has served as a reference gene in the conventional qPCR for telomere measurement in the art (9). However, when analyzed for single cell amplification, 36B4 did not produce robust results as determined by the melting curve of 36B4 amplicons by qPCR performed following multiplex PCR of a single cell of the human epithelial carcinoma cell line HeLaS3 and of the mouse tail tip fibroblasts (TTF); the melting curve of 36B4 amplicons for both the mouse and human analysis from a single cell frequently showed multiple peaks (FIGS. 1B and 1C). In contrast, a very robust telomere DNA amplification was noted (FIGS. 1B and 1C). This suggested that a single copy gene from a single cell may be unavailable for amplification under such restrictive conditions.

Multi-copy genes, some with thousands of copies of sequences throughput the genome, a characteristic similar to telomeres, were thought to provide a more dependable amplification when using genomic material of a single cell. Three multi-copy genes, Alu (human), 18srDNA (human) and B1 (mouse) were tested as reference genes and attained robust results of single cell amplification as determined by the clean single peaks for the melting curve of each multi-copy gene amplicon (FIGS. 1B and 1C).

Figure 2B:
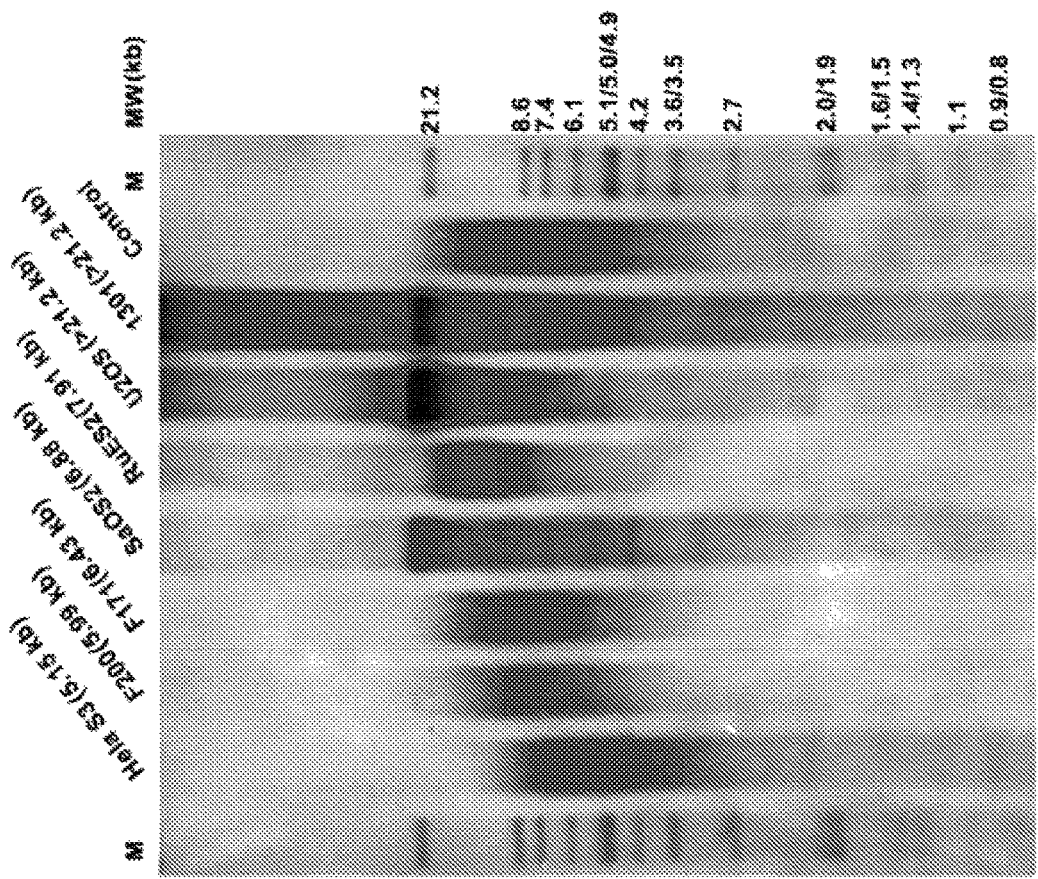
FIGS. 2A and 2B show the measurement of telomere length of various human cell populations by qPCR and TRF.
Figure 2A:
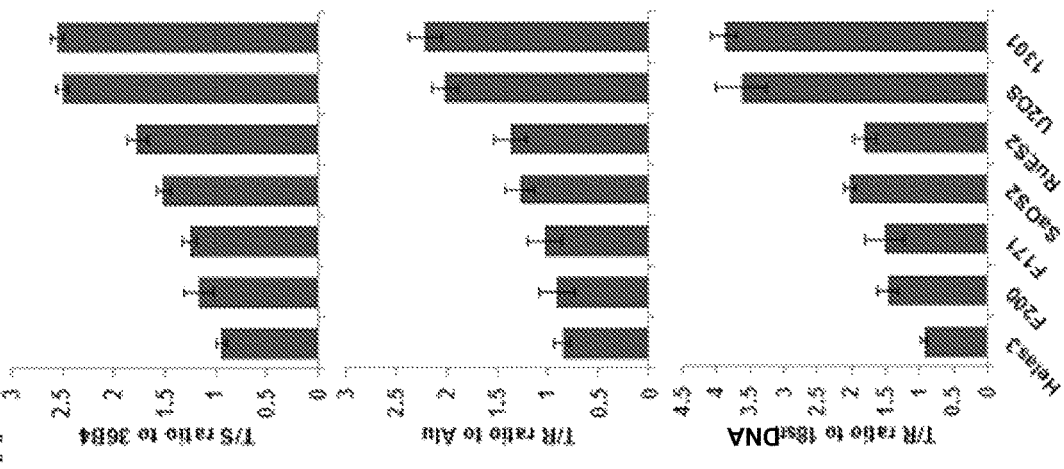

Relative telomere lengths were subsequently determined with a ratio of telomere length to reference gene length (T/R) using multi-copy gene Alu or 18srDNA following the novel multiplex PCR-qPCR protocol for various human cell populations. The ratios were consistently found to correlate with those utilizing the single copy gene 36B4 (FIG. 2A). The correlation between multi-copy Alu and single copy 36B4 was determined to be $R^2=0.9836$ and $R^2=0.9527$ between multi-copy 18srDNA and 36B4 (FIGS. 1D and E).

Figure 1E:
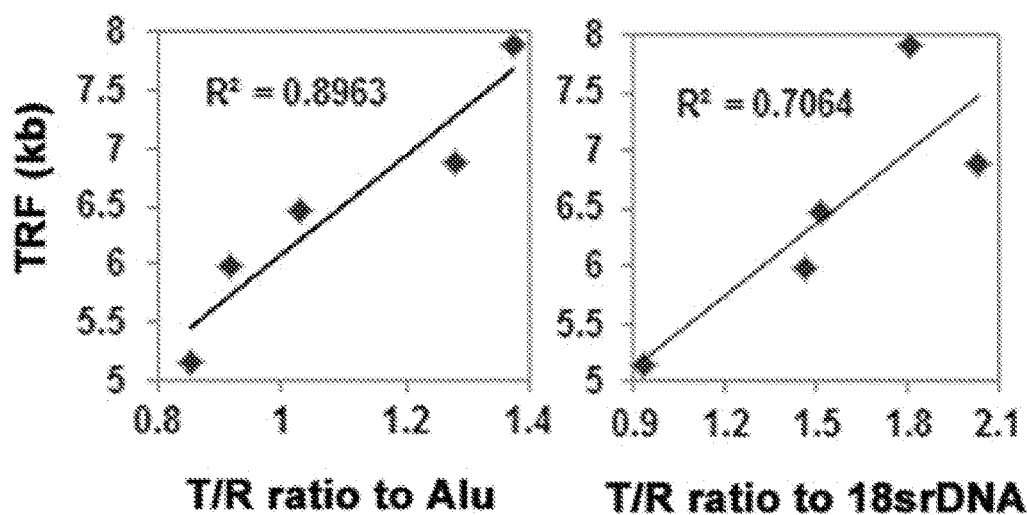

The telomere restriction fragment (TRF) method was also utilized to measure the absolute telomere length in various human cell lines. The known standard protocol requiring a large cell population was performed. The telomere length of human cell lines by TRF using a large sample size was found to be proportional to the T/R ratios determined with the novel SCT-pqPCR protocol; the multi-copy gene Alu showed a slightly better correlation using TRF with the single copy 36B4 ($R^2=0.8963$) as compared to 18srDNA ($R^2=0.7064$) (FIGS. 1E and F). The multi-copy gene Alu was hence chosen for further telomerase length analysis in human cells. Similarly, the multi-copy B1 sequence was utilized as the reference gene for single cell telomere analysis in mouse cells.

Figure 1F:
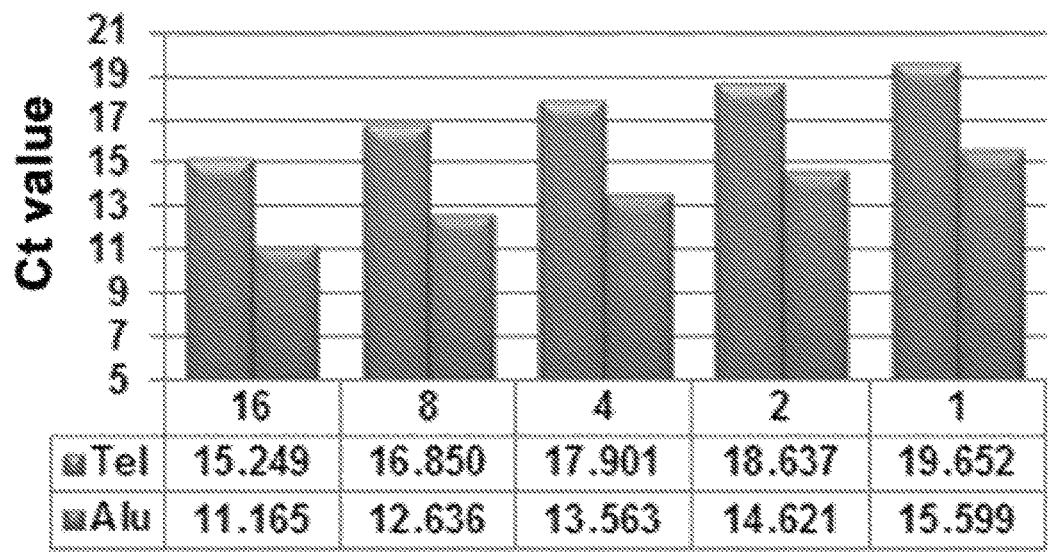
Figure 1G:
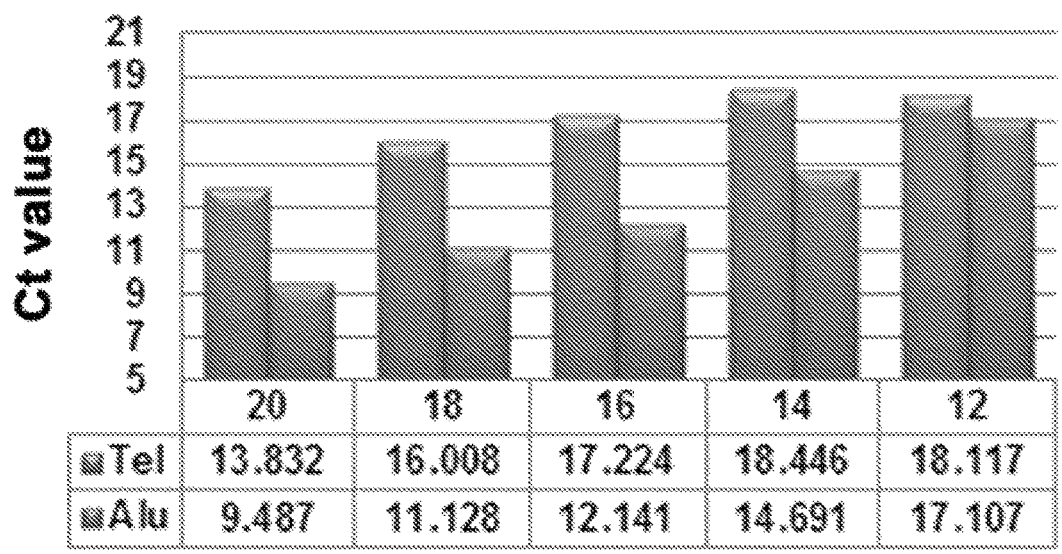
Figure 3A:
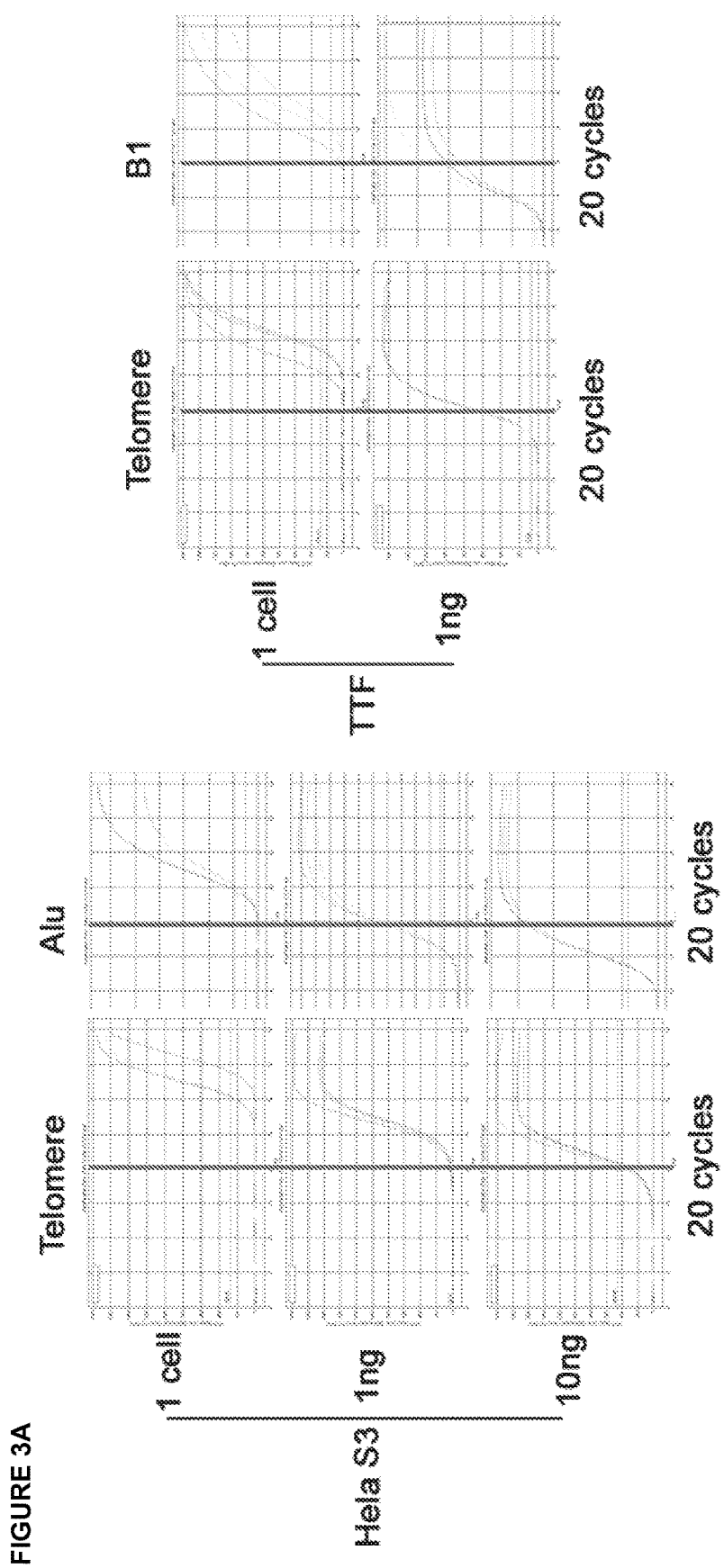
FIGS. 3A and 3B depict the amplification analysis of genomic DNA and the resulting standard curves based on primers for human and mouse DNA.

DNA amounts of up to 10 ng were achieved from a single HelaS3 cell. Use of this amount of DNA resulted in a plateau of PCR amplification product when the cycle number was over 20 regardless of the primers which were used. Mouse TTF showed a similar result in that a plateau was reached when over 20 cycles of PCR were performed (FIG. 3A). Single cell DNA of human lung fibroblasts were pre-amplified using telomere and Alu primers simultaneously for 20, 18, 16, 14 or 12 cycles. The Ct values were proportionally increased with each decreasing cycle number starting from cycle 18 to cycle 14 (FIG. 1G).

Figure 3B:
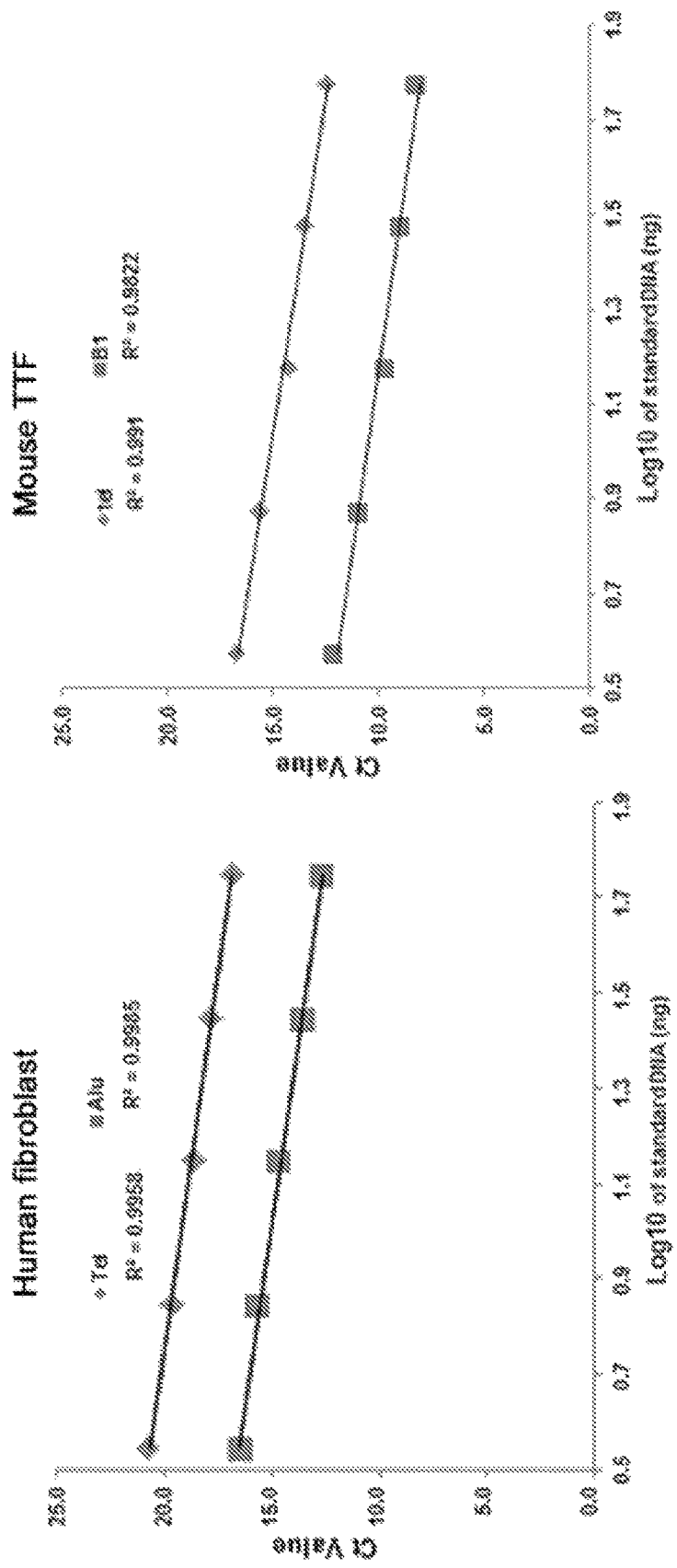

The multiplex PCR step required optimization of the number of cycles which would yield the functional Ct values and a loyal amplification product that can be used in the second round of the novel protocol, qPCR. Standard curves for telomere and the reference genes were defined by amplifying a series of dilutions of genomic DNA. The standard curves were determined to be linear within the DNA concentrations of 1 ng/μl to 16 ng/μl for human cells (FIG. 3B, left panel) and 0.375 ng/μl to 6 ng/μl for mouse cells (FIG. 3B, right panel).

The Ct values of standard DNA and those following various pre-PCR cycles were compared (FIGS. 1F and G) to indicate that the amplification obtained from pre-PCR cycles 16 to 18 were optimal. The telomere length of mouse is known to be generally longer than that of human, and expectedly requires fewer cycles for amplification. Hence, taken together, 17 and 16 cycles were chosen for the multiplex PCR step for human and mouse cells, respectively. It is noted the T/R ratio obtained for mouse telomeres cannot be directly compared with the T/R ratio for human telomeres due to the differences in length and pre-amplification protocol. To overcome this dissimilarity, a correlation of T/R ratio measured by SCT-pqPCR with TRF (kb) by Southern blot should be established initially using a cell population for each species by each individual laboratory.

Ct value and amplification efficiency of standard DNA with low concentration in human fibroblast (the mean of three repeat raw data.)

| DNA (ng/μl) | Ct value of primers | |
|---|---|---|
| | Tel | Alu |
| 2.000 | 19.328 | 15.108 |
| 1.000 | 21.184 | 16.783 |
| 0.500 | 22.105 | 17.797 |
| 0.250 | 27.122 | 22.621 |
| 0.125 | 29.965 | 26.408 |
| Efficiency | 29.0% | 27.6% |

Ct value and amplification efficiency of standard DNA with low concentration in mouse TTF (the mean of three repeat raw data.)

| DNA (ng/μl) | Ct value of primers | |
|---|---|---|
| | Tel | B1 |
| 3.000 | 14.260 | 9.650 |
| 1.500 | 15.670 | 10.840 |
| 0.750 | 16.770 | 12.140 |
| 0.375 | 19.480 | 14.890 |
| 0.188 | 25.050 | 21.170 |
| Efficiency | 29.2% | 31.4% |

Example 2: Average Telomere Length Estimated by SCT-pqPCR as Compared to Conventional Methods of Different Cell Populations Methods QPCR Assay for Average Telomere Measurement of a Population of Cells:

Average telomere length was measured from total genomic DNA of human cell lines by using the qPCR method previously described (9). The methods from each are hereby incorporated by reference. First, the same protocol was followed and the single copy gene 36B4 chosen as the reference. Multi-copy genes Alu and 18srDNA were chosen as reference genes and the average telomere length of different human cell lines were measured. Each reaction included 10 μl 2×SYBR Green mix (Bio-Rad), 0.5 μl each of 10 μM forward and reverse primers, 4 μl molecular-filter water and 5 μl genomic DNA (7 ng/μl) to yield a 20 μl reaction. DNA samples were placed in three adjacent wells of a 96-well plate for telomere primers and reference gene primers. A Bio-Rad thermocycler (CFX system test) was used with reaction conditions of 95° C. for 10 min followed by 40 cycles of data collection at 95° C. for 15 seconds, 60° C. anneal for 30 seconds and 72° C. extend for 30 seconds along with 80 cycles of melting curve from 60° C. to 95° C. To serve as a reference for standard curve calculation, mouse TTF and human fibroblast were serially diluted and qPCR performed as described above. After thermal cycling completion, the CFX manager software was used to generate standard curves and Ct values for telomere signals and reference gene signals. Here different reference genes were used for telomere length measurement, and each sample of DNA had one telomere signal (T) and reference gene signal (R). The average telomere length was termed the T/R ratio.

Telomere QFISH:

Telomere QFISH and quantification were performed as described previously in 11, 22. The methods from each are hereby incorporated by reference.

Cell and Embryo Culture:

The 1301 cell line (T-cell leukemia, Sigma, #01051619) was cultured in RPMI medium 1640 (Invitrogen) supplemented with 10% FBS, 2 mM Glutamine (Invitrogen), 100 U/ml penicillin and 100 µg/ml streptomycin (Invitrogen). U2OS cell (ATCC HTB-96) and SaOS2 cell (ATCC HTB-85) were cultured in McCoy's 5a Medium (ATCC 30-2007) supplemented with 15% FBS. Human embryonic stem cell Rues2 (Rosa et al., Developmental Cell., 2009, 16(4):517-527) was cultured in Nutristem SF/FF culture medium (Stemgent) with 12 ng/ml bFGF (Invitrogen) on Matrigel.

DNA Extraction of a Population of Cells:

Genomic DNA of cell populations (about $5\times10^5$ cells of each cell line) was extracted by the Tissue and Blood DNA extraction kit (Qiagen) as per the instructions. The resulting concentration of DNA was measured with Nanodrop (FIG. 4). Table I summarizes these comparison findings. U2OS and SaOS2 are human osteosarcoma cell lines, RuES2 is human embryonic stem cell and F171 and F200 are human lung fibroblasts from 14 weeks gestation and a 71-year old male donor respectively.

TABLE I

Comparison of relative telomere length between human cell populations and single cells by various methods:

| Cell line | Mean T/R ratio of single cell | Relative fluorescence intensity by QFISH | T/S ratio of population cells | TRF(kb) of population cells |
|---|---|---|---|---|
| F171 | 0.826 | 422.625 | 1.261 | 6.464 |
| F200 | 0.681 | 249.855 | 1.166 | 5.989 |
| HelaS3 | 0.679 | 339.53 | 0.946 | 5.148 |
| RuES2 | 1.274 | 578.253 | 1.771 | 7.906 |
| SaOS2 | 1.202 | 625.677 | 1.523 | 7.344 |
| U2OS | 1.763 | 1550.925 | 2.507 | >21.2 |

* T/S ratio is telomere sequence relative to single copy gene 36B4

Raw data for Table I:

| cycle number | single cell | Ct value of Tel | | | Ct value of Alu | | | Ct value of 18srDNA | | |
|---|---|---|---|---|---|---|---|---|---|---|
| 20 | sc1 | 13.796 | 13.699 | 13.584 | 9.422 | 9.375 | 9.444 | 14.368 | 14.458 | 14.460 |
|  | sc2 | 13.671 | 13.737 | 13.704 | 9.192 | 9.186 | 9.180 | 14.807 | 14.765 | 14.716 |
|  | sc3 | 13.679 | 13.964 | 14.103 | 9.657 | 9.612 | 9.662 | 13.308 | 13.318 | 13.266 |
|  | sc4 | 14.109 | 13.967 | 13.976 | 9.744 | 9.677 | 9.692 | 14.269 | 14.301 | 14.288 |
| 18 | sc1 | 15.617 | 15.586 | 15.480 | 11.247 | 11.227 | 11.226 | 16.214 | 16.216 | 16.184 |
|  | sc2 | 15.505 | 16.165 | 15.865 | 11.049 | 11.107 | 11.306 | 15.551 | 15.608 | 17.570 |
|  | sc3 | 16.255 | 16.133 | 16.083 | 11.015 | 10.907 | 10.823 | 16.715 | 16.656 | 16.656 |
|  | sc4 | 16.471 | 16.527 | 16.403 | 11.283 | 11.142 | 11.201 | 17.051 | 17.098 | 17.169 |
| 16 | sc1 | 17.236 | 17.274 | 17.230 | 11.931 | 11.930 | 12.219 | 17.571 | 17.586 | 17.601 |
|  | sc2 | 17.572 | 17.453 | 17.483 | 12.606 | 12.628 | 12.607 | 17.373 | 17.415 | 17.389 |
|  | sc3 | 17.073 | 17.039 | 17.039 | 11.766 | 12.070 | 11.757 | 18.417 | 18.398 | 18.469 |
|  | sc4 | 17.028 | 17.002 | 17.261 | 11.977 | 12.001 | 12.195 | 17.876 | 17.886 | 17.880 |
| 14 | sc1 | 18.609 | 18.736 | 18.974 | 14.799 | 14.782 | 14.749 | 19.564 | 19.593 | 19.542 |
|  | sc2 | 18.411 | 18.375 | 18.458 | 14.584 | 14.688 | 14.900 | 20.137 | 20.086 | 20.113 |
|  | sc3 | 18.362 | 18.261 | 18.309 | 15.130 | 14.476 | 14.779 | 20.360 | 20.282 | 20.289 |
|  | sc4 | 18.176 | 18.385 | 18.296 | 14.441 | 14.541 | 14.428 | 19.106 | 19.088 | 19.208 |
| 12 | sc1 | 18.461 | 18.502 | 18.307 | 17.325 | 17.417 | 17.625 | 21.750 | 20.917 | 21.684 |
|  | sc2 | 16.677 | 16.925 | 17.192 | 16.455 | 16.103 | 16.535 | 19.835 | 20.466 | 19.613 |
|  | sc3 | 18.781 | 19.184 | 18.955 | 17.377 | 17.229 | 17.620 | 22.983 | 22.928 | 22.865 |
|  | sc4 | 18.277 | 18.082 | 18.057 | 17.016 | 16.999 | 17.582 | 21.685 | 21.621 | 21.976 |

(Thermo) using a 10-fold diluted aliquot of DNA. To measure the average of telomere length, the concentrations of DNA were diluted to 4 ng/µl for mouse samples and 7 ng/µl for human samples in molecular-filtered water. Seven concentrations of standard DNA spanning a 64-fold range were prepared by serial dilution from 0.1875 ng/µl to 12 ng/µl for mouse TTF. Eight concentrations of standard DNA spanning a 128-fold range were diluted from 0.125 ng/µl to 16 ng/µl for human fibroblasts.

Results

Figure 5:
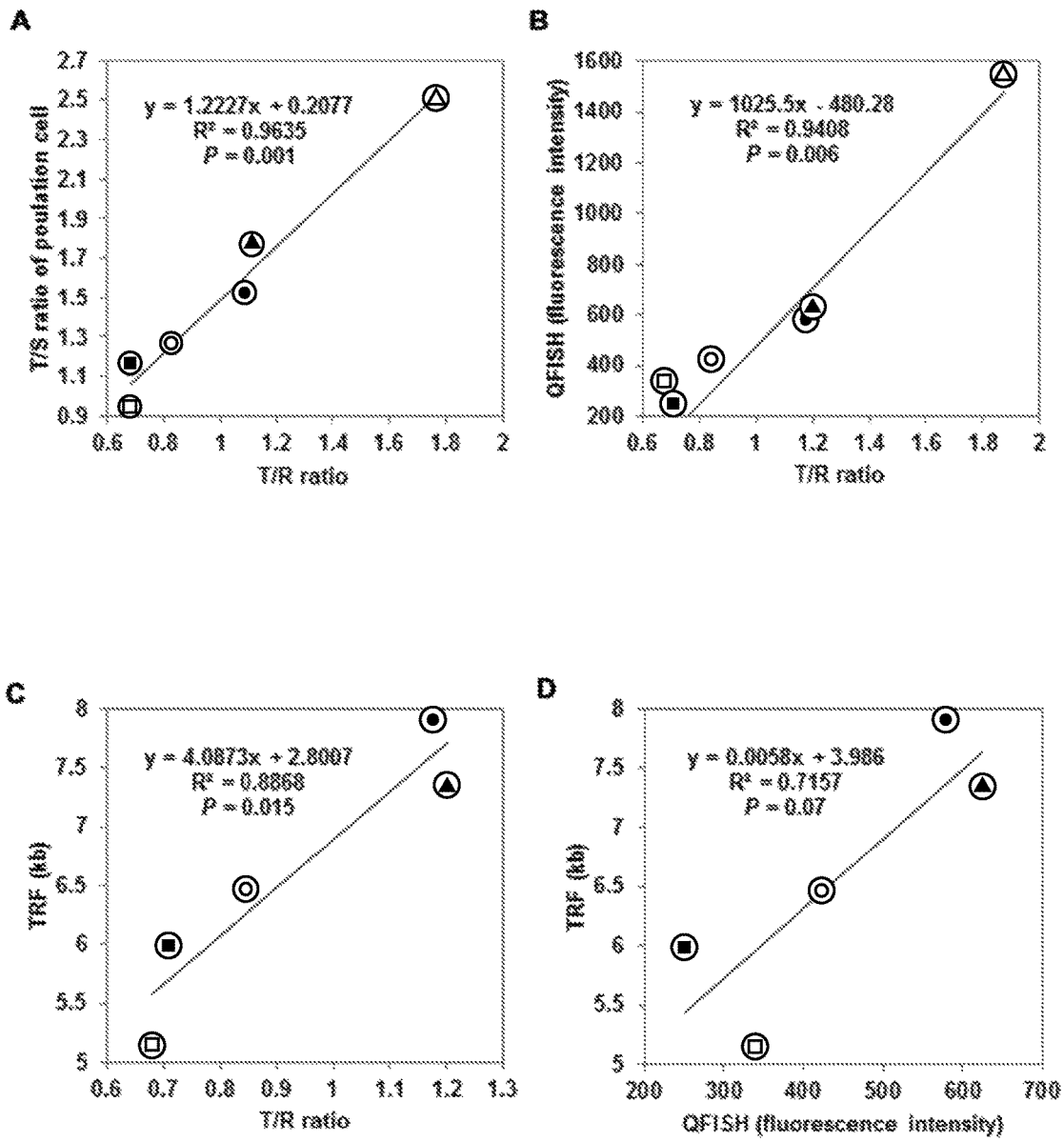
FIGS. 5A-5D presents the linear correlation of relative telomere length between individual cells and populations of various human cell lines when using SCT-pqPCR as compared to qPCR, TRF and QFISH.

The present two tier PCR analysis was validated by a comparison analysis in which the average telomere length calculated using single cell measurements by SCT-pqPCR was paralleled to established methods including qPCR, QFISH and TRF. Using the aforementioned analysis parameters established for SCT-pqPCR, the average telomere length of single cells measured by SCT-pqPCR in human cell lines, F171, F200, HelaS3, RuES2, U2OS and SaOS2 was compared to the telomere length of this population of cells measured by conventional qPCR (FIG. 2A) and QFISH The single cell telomere length data deduced by SCT-pqPCR was shown to correlate significantly with the average telomere length of these cell populations as measured by the well-established methods of qPCR and QFISH. The strong correlation was defined by the Pearson test which produced P values of 0.001 and 0.006 when comparing qPCR and QFISH, respectively (FIGS. 5A and B). The novel SCT-pqPCR was further correlated to the established TRF protocol in these human cell lines; the Pearson test once again showed that the average of the single cell telomere lengths as measured by SCT-pqPCR highly correlated with the absolute telomere length determined by TRF, with a P value of 0.015 (FIG. 5C). Surprisingly, a lower correlation between QFISH and TRF was found in these 5 cell lines with a P value of 0.07 (FIG. 5D).

Figure 6:
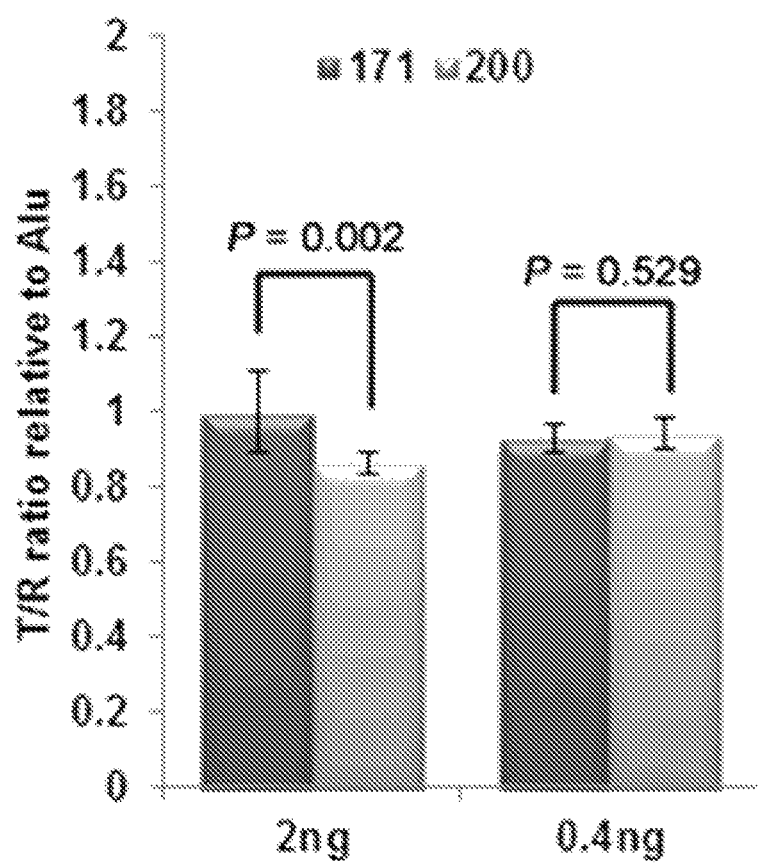
FIG. 6 is a bar graph showing the T/R ratio of telomeres in primary human cells using Alu as the reference gene and 12 cycles during pre-PCR.

It has been presumed that the heterogeneity of single cell telomere lengths in cancer cell lines exceeds that of normal cell lines. Further, variations in telomere lengths between cycling and quiescent cells may bias QFISH results due to the nature of the assay; QFISH measures only telomere lengths of dividing cells capable of arresting at metaphase, while the TRF and qPCR methods measure average telomere length of all cells. This discrepancy further supports the value of this novel SCT-pqPCR method for telomere measurement of individual cells performed independently of replication rate or potential. The SCT-pqPCR was further validated by deduction of telomere lengths in dilutions of pre-amplified DNA of cell lines F171 and F200, human lung fibroblast from a 14-week gestation and a 71-year old donor respectively, following pre-amplification of DNA with target primers to telomere and the reference gene Alu. Input DNA of 2 ng resulted in the relative telomere length in F171 as being longer than that of F200. However, upon decreasing the DNA quantity to 0.4 ng, no significant difference in telomere lengths between fibroblast F171 and F200 was noted, P>0.05 (FIG. 6). Therefore it was deduced that when the pre-purified DNA drops below the threshold value, one aliquot of diluted DNA does not fairly represent the entire genome. The approximately 0.5 ng to 1 ng threshold for purified human genome DNA has been observed in a whole genome amplification effort (19, 20). The locus representation was significantly distorted in the instances that input gDNA aliquoted from a large DNA pool was <0.5 to 1 ng. Alternatively, an intact single cell, although it contains only about 6-7 pg DNA, contains an entire set of genomic sequences including all telomeres.

Example 3: Further Validation of Single Cell Telomere Length Measurements by SCT-pqPCR Methods Cell and Embryo Culture:
Mouse ES cells were cultured on a feeder layer with Knockout DMEM (Invitrogen) supplemented with 20% FBS, 1000 U/ml leukemia inhibitory factor (LIF) (ESGRO, Chemicon), 0.1 mM nonessential amino acids (Sigma), 0.1 mM β-mercaptoethanol (Invitrogen), 2 mM GlutaMAX (Invitrogen) and 100 U/ml penicillin and 100 µg/ml streptomycin. Mouse zygotes were ordered from Embryotech laboratories and stored in liquid nitrogen. KSOM (Millipore) was made according to the manufacturer's protocol. Mouse zygotes were thawed and cultured in KSOM drops with oil according to the manufacturer's instruction. The 2-cell and 4-cell embryos were obtained by culture of zygotes in KSOM for 1 day and 2 days respectively. Human GV oocytes were cultured in HTF.

Single Cell Isolation and Lysis:
Mouse embryos were digested with 0.5% Pronase (Calbiochem) in the KSOM media in which they were grown to eliminate the zona pellucida. After washing three times in 0.1% PVP/PBS (0.22 µm filter), the zygotes without zona pellucida were picked up in 1 µl PVP/PBS and placed in a 0.2 ml PCR tube. The 2-cell and 4-cell mouse embryos without zona pellucida were placed into drops of 0.25% Trypsin-EDTA and incubated at 37° C. for 10 min, and then dispersed to individual cells by mechanical pipetting up and down. The individual cells were transferred into 0.1% PVP/PBS and washed 3 times with 0.1% PVP/PBS. The single sister cells of 2-cell and 4-cell embryos were picked up with 1 µl buffer each and delivered in a 0.2 ml PCR tube.

Human mature oocytes were individually treated with 0.5% Pronase in modified HTF (mHTF, Irvine Scientific) for 1-3 minutes until the zona pellucida began to thin when viewed under the dissecting microscope. Oocytes with thin zona pellucida were quickly washed through three subsequent washes of mHTF. The oocyte and polar body were separated by mechanical pipetting up and down within the last wash drop. Occasionally, separation was aided by returning oocyte and polar body to the incubator for 1-2 hours prior to mechanical separation. Polar bodies were picked up first followed by the matched oocyte to reduce risk of polar body loss in the last wash drop.

Figure 11:
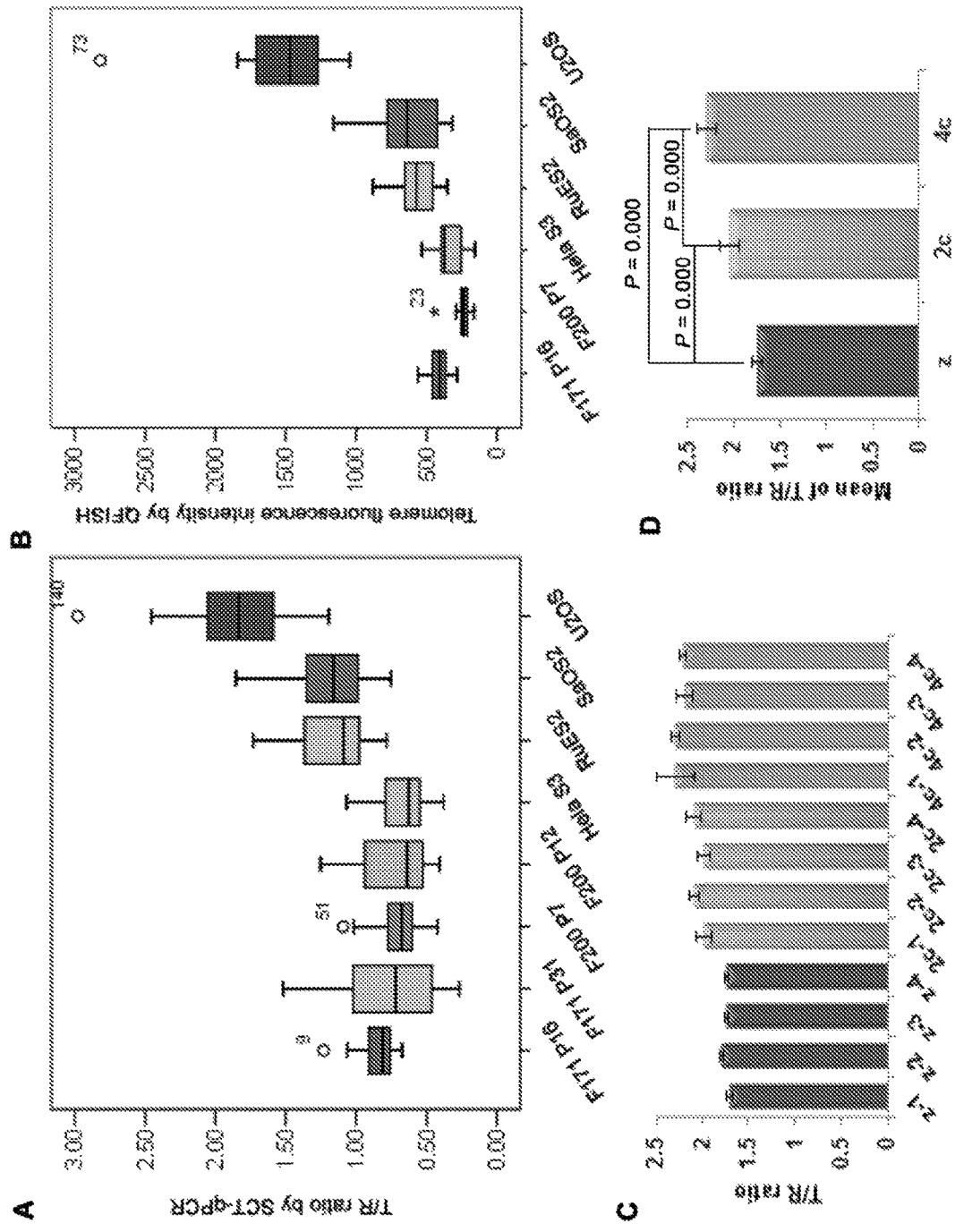
FIGS. 11A-11D depict the variations of telomere length in single cells of different cell lines or primary cells.

To obtain daughter cells from HelaS3, a single cell was selected into one drop on the 35 mm petri-dish prepared with HelaS3 cell culture medium (FIG. 11). After 24 hours, the drops containing 2 daughter cells were selected and placed into a 0.2 ml PCR tube with 1 µl PBS buffer.

Results

Figure 7A:
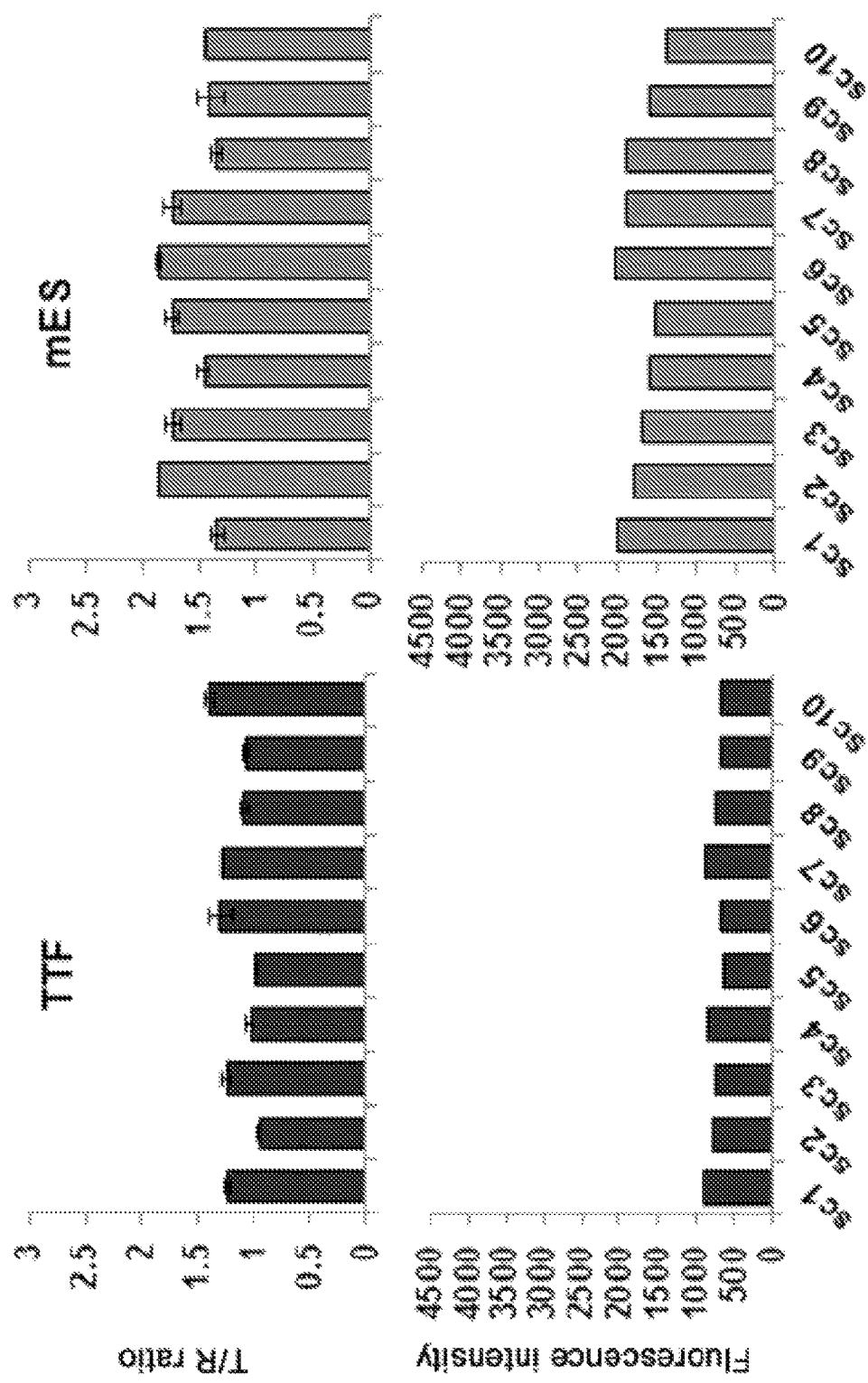
FIGS. 7A-7F show the analysis of the measurement of relative telomere length (T/R ratio) by SCT-pqPCR.

In order to validate single cell telomere length measurements using the novel method of the invention, two human cell types with known different telomere lengths were chosen: HelaS3 and 1301, a T-cell leukemia, human cell lines with average telomere lengths of 5 kb (15) and 70 kb, respectively. Further, two mouse cell lines with different telomere lengths were also analyzed: embryonic stem cells (ESC) and tail tip fibroblasts (TTF) (21). The telomere length of single cells in the same population of these lines was found to vary by SCT-pqPCR analysis; these results were consistent with the QFISH telomere length analyses (FIGS. 7A, B, E, and F). The calculated average telomere length of multiple single cells was significantly longer in mESCs than in TTF of mice, and longer in 1301 human cells than in HelaS3 by SCT-pqPCR, as expected.

Figure 7B:
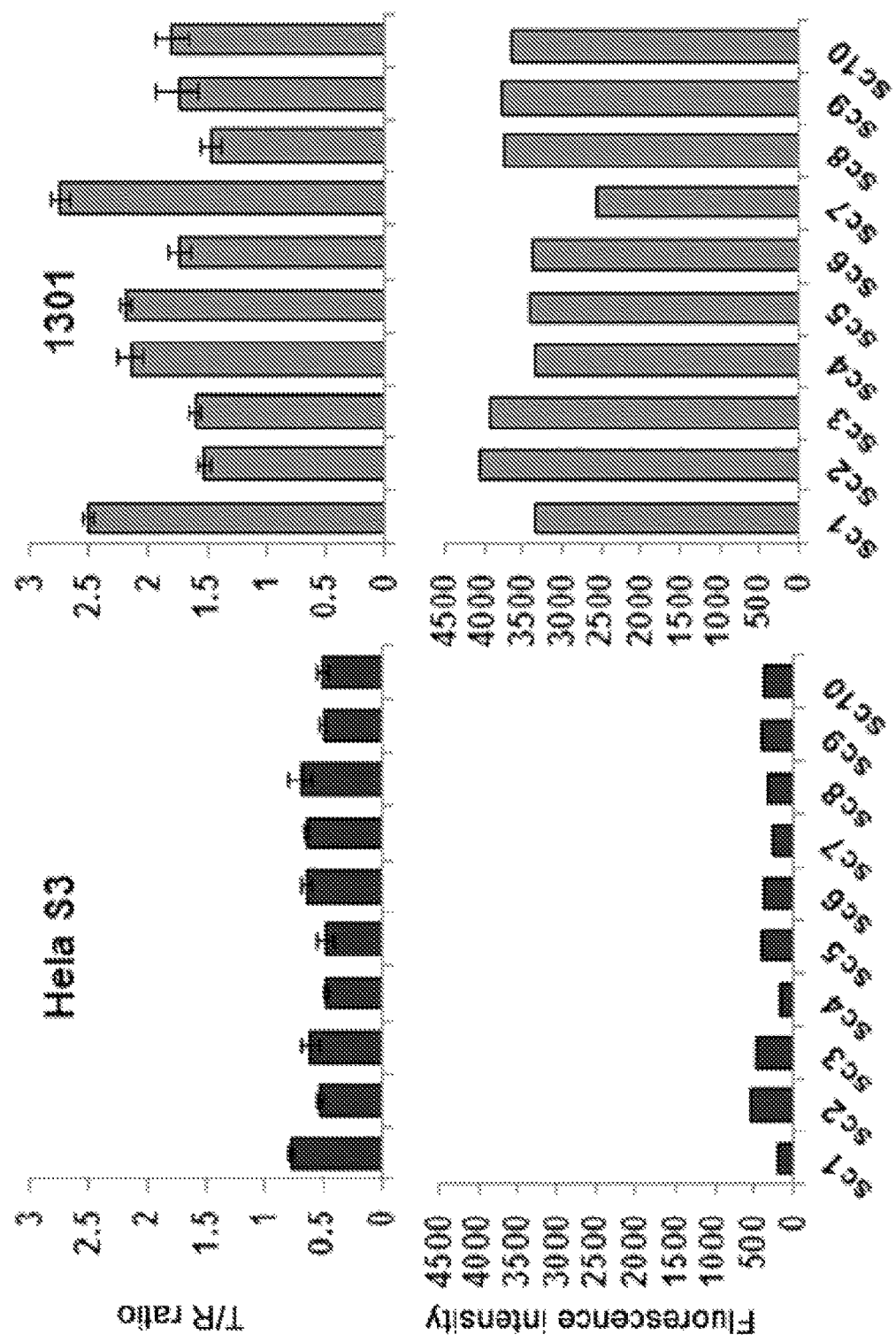
Figure 7C:
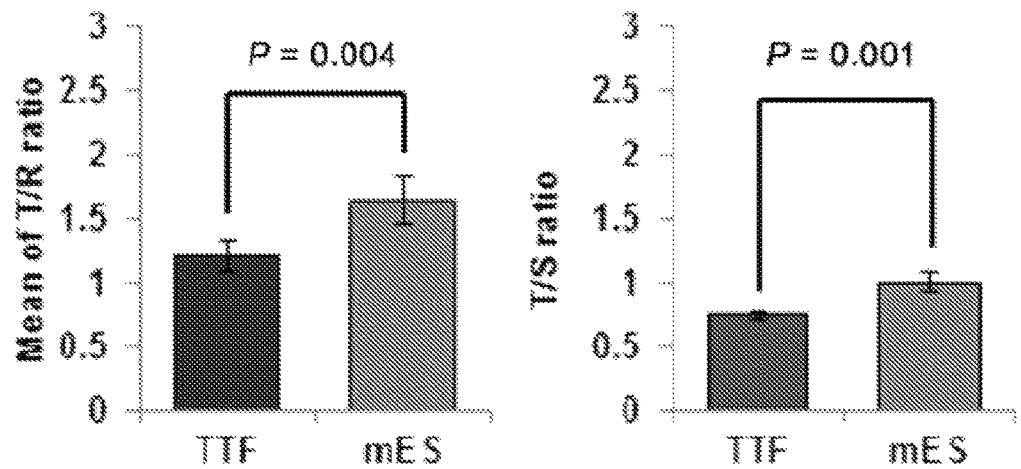
Figure 7D:
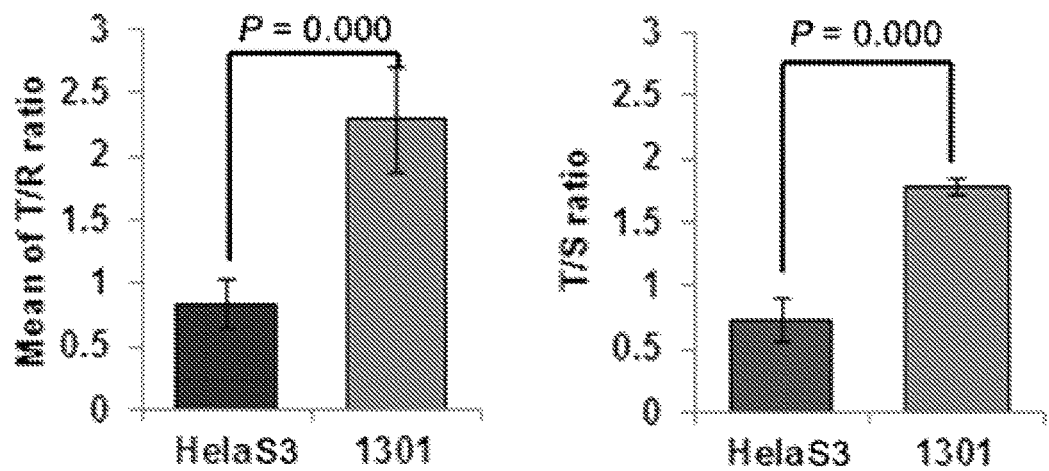
Figure 7E:
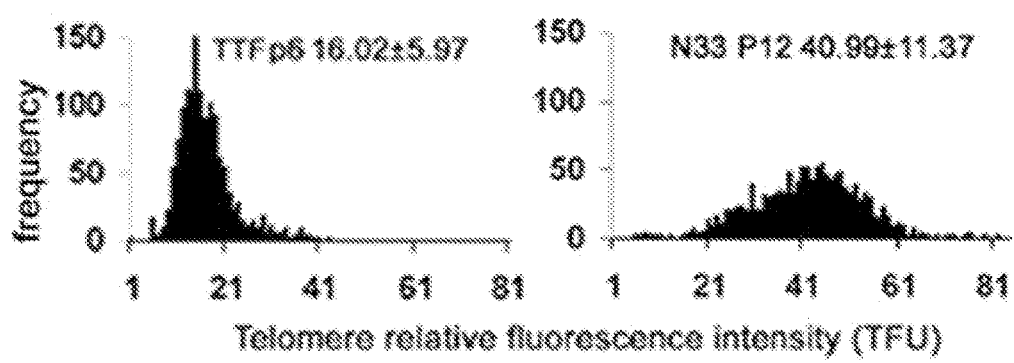
Figure 7F:
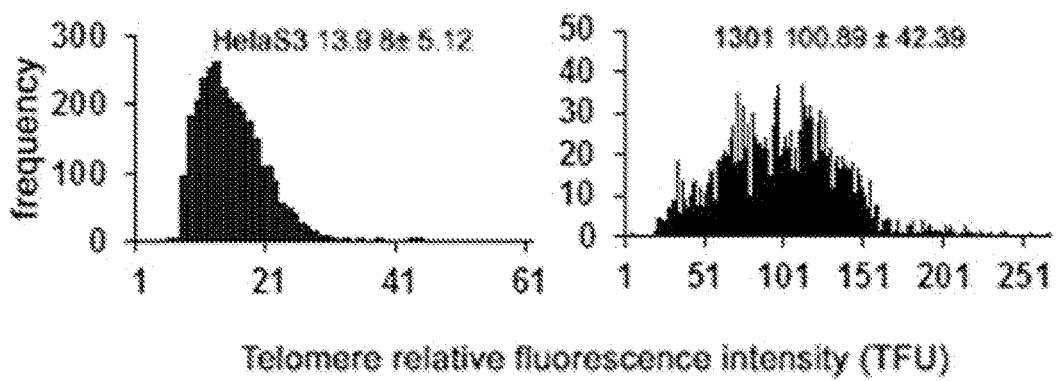

Single cell telomere length variations were identified by both SCT-pqPCR and also by QFISH utilizing independent samples T test. The average T/R ratio of single cells measured by SCT-pqPCR was consistent with that of a cell population measured by SCT-pqPCR (T/R) and also as measured by conventional qPCR (T/S, single copy gene 36B4) (FIGS. 7B and E).

Authentication of this novel PCR assay would require the measure of telomere length in the same individual cell or clone by two different assays. The limitation for the aforementioned validation step was that SCT-pqPCR and QFISH could not be performed on the same individual cells; further, no somatic cells with identical telomere lengths could be reliably identified for this validation. Hence, telomere length was measured in a pair of sister cells derived from two-cell mouse embryos and oocytes. Two-cell mouse embryos exhibit identical telomere lengths between sister blastomeres (22). Further, human polar bodies (PBs) show telomere lengths nearly identical to their matched MII oocytes by QFISH analysis (23).

Telomere lengths were observed to be remarkably similar between sister blastomeres by SCT-pqPCR, P>>0.1 as shown in Table II. However, the one-way ANOVA (Tukey test) did indicate that differences existed between pairs of sister cells from different embryos (FIG. 8).

TABLE II

Telomere length between pairs of mouse 2-cell embryo sister cells, human oocyte and polar body and daughter cells of HelaS3 by SCT-pqPCR.

| Samples | Mean of T/R ratio | Std. Deviation | P value |
| --- | --- | --- | --- |
| 2cell 1-1 | 1.895 | 0.043 | 0.425 |
| 2cell 1-2 | 2.018 | 0.066 | |
| 2cell 2-1 | 1.539 | 0.061 | 0.523 |
| 2cell 2-2 | 1.678 | 0.046 | |
| 2cell 3-1 | 1.673 | 0.064 | 0.982 |
| 2cell 3-2 | 1.687 | 0.061 | |
| 2cell 4-1 | 1.986 | 0.09 | 0.608 |
| 2cell 4-2 | 2.089 | 0.052 | |

TABLE II-continued

Telomere length between pairs of mouse 2-cell embryo sister cells, human oocyte and polar body and daughter cells of HelaS3 by SCT-pqPCR.

| Samples | Mean of T/R ratio | Std. Deviation | P value |
|---|---|---|---|
| 2cell 5-1 | 1.569 | 0.039 | 0.777 |
| 2cell 5-2 | 1.454 | 0.03 | |
| 2cell 6-1 | 1.468 | 0.049 | 0.407 |
| 2cell 6-2 | 1.564 | 0.104 | |
| 2cell 7-1 | 1.69 | 0.035 | 0.883 |
| 2cell 7-2 | 1.619 | 0.041 | |
| 2cell 8-1 | 1.604 | 0.063 | 0.582 |
| 2cell 8-2 | 1.838 | 0.078 | |
| 2cell 9-1 | 1.661 | 0.022 | 0.639 |
| 2cell 9-2 | 1.728 | 0.027 | |
| 2cell 10-1 | 1.609 | 0.027 | 0.872 |
| 2cell 10-2 | 1.592 | 0.027 | |
| 2cell 11-1 | 1.843 | 0.065 | 0.175 |
| 2cell 11-2 | 1.704 | 0.151 | |
| 2cell 12-1 | 1.986 | 0.073 | 0.854 |
| 2cell 12-2 | 2.091 | 0.079 | |
| Polar body 1 | 0.875 | 0.013 | 0.005 |
| Oocyte 1 | 0.819 | 0.007 | |
| Polar body 2 | 0.843 | 0.021 | 0.905 |
| Oocyte 2 | 0.835 | 0.107 | |
| Polar body 3 | 0.77 | 0.008 | 0.664 |
| Oocytes 3 | 0.773 | 0.007 | |
| Polar body 4 | 0.885 | 0.031 | 0.312 |
| Oocyte 4 | 0.847 | 0.048 | |
| Polar body 5 | 0.805 | 0.054 | 0.54 |
| Oocyte 5 | 0.828 | 0.022 | |
| Polar body 6 | 1.145 | 0.004 | 0 |
| Oocyte 6 | 1.268 | 0.002 | |
| Polar body 7 | 1.149 | 0.014 | 0.101 |
| Oocyte 7 | 1.198 | 0.004 | |
| HelaS3 1-1 | 0.634 | 0.018 | 0 |
| HelaS3 1-2 | 0.845 | 0.021 | |
| HelaS3 2-1 | 0.577 | 0.015 | 0.002 |
| HelaS3 2-2 | 0.751 | 0.042 | |
| HelaS3 3-1 | 0.625 | 0.038 | 0.012 |
| HelaS3 3-2 | 0.747 | 0.03 | |
| HelaS3 4-1 | 0.502 | 0.027 | 0.888 |
| HelaS3 4-2 | 0.507 | 0.059 | |
| HelaS3 5-1 | 0.291 | 0.013 | 0.009 |
| HelaS3 5-2 | 0.402 | 0.038 | |
| HelaS3 6-1 | 0.679 | 0.022 | 0.037 |
| HelaS3 6-2 | 0.797 | 0.063 | |
| HelaS3 7-1 | 0.747 | 0.031 | 0.01 |
| HelaS3 7-2 | 0.876 | 0.036 | |
| HelaS3 8-1 | 0.638 | 0.026 | 0.273 |
| HelaS3 8-2 | 0.66 | 0.014 | |
| HelaS3 9-1 | 0.718 | 0.036 | 0 |
| HelaS3 9-2 | 0.944 | 0.005 | |
| HelaS3 10-1 | 1.015 | 0.011 | 0.051 |
| HelaS3 10-2 | 1.078 | 0.038 | |

Figure 8A:
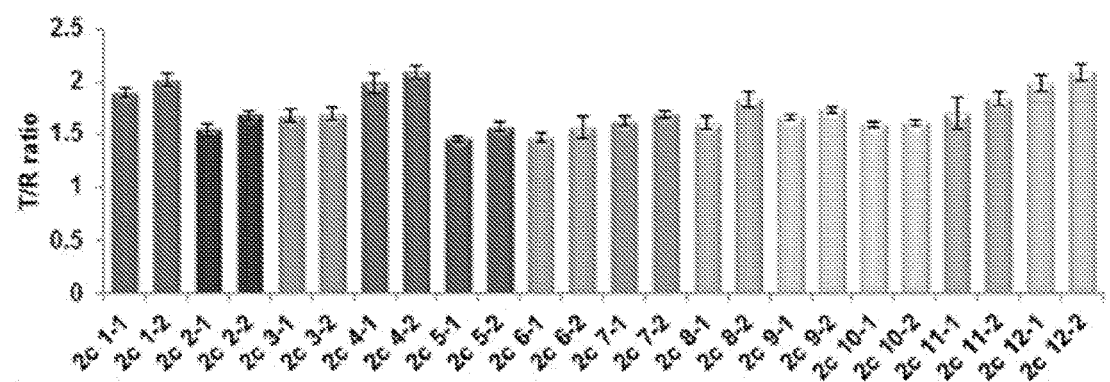
FIGS. 8A-8F present the measurements of telomere length in mouse 2-cell stage embryos and in pairs of human oocytes and polar bodies determined by SCT-pqPCR.
Figure 8B:
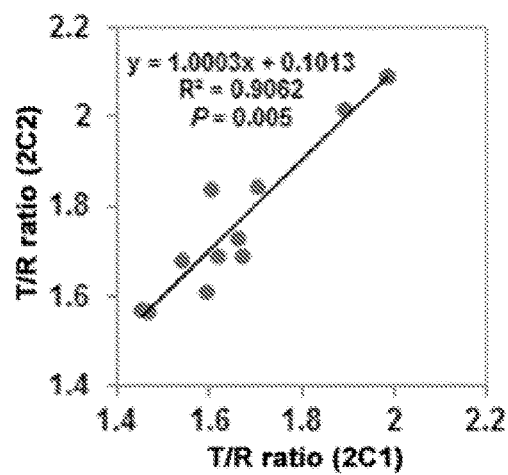
Figure 8C:
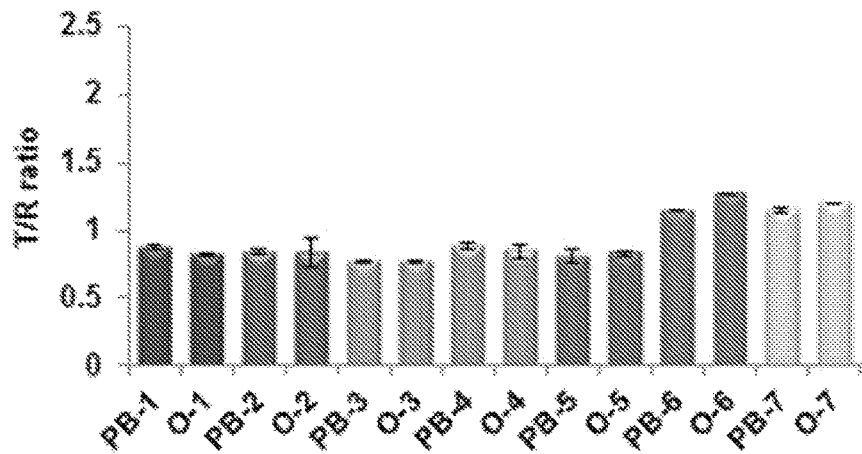
Figure 8D:
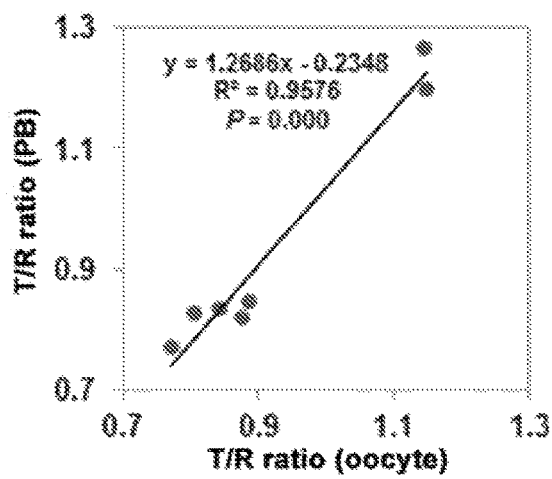
Figure 8E:
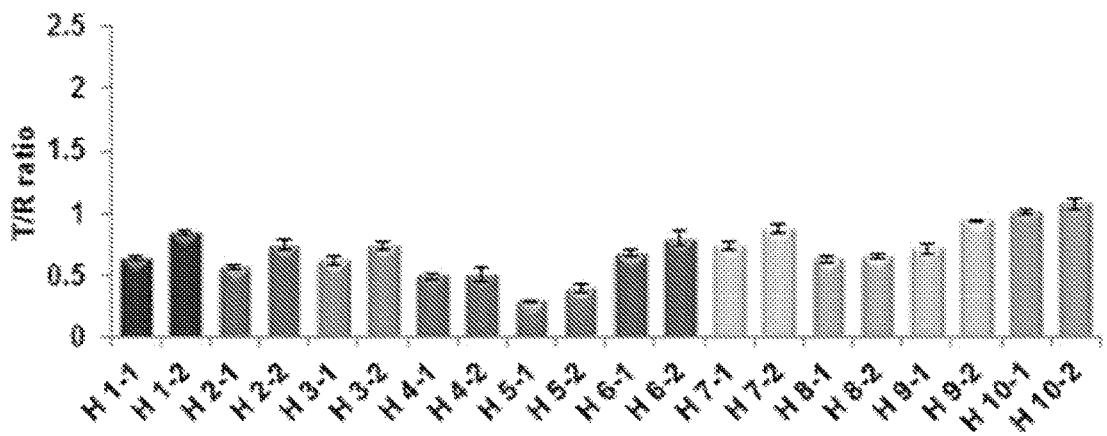
Figure 8F:
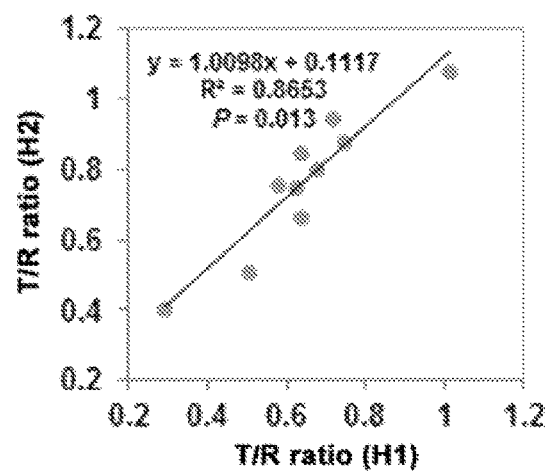
Figure 9:
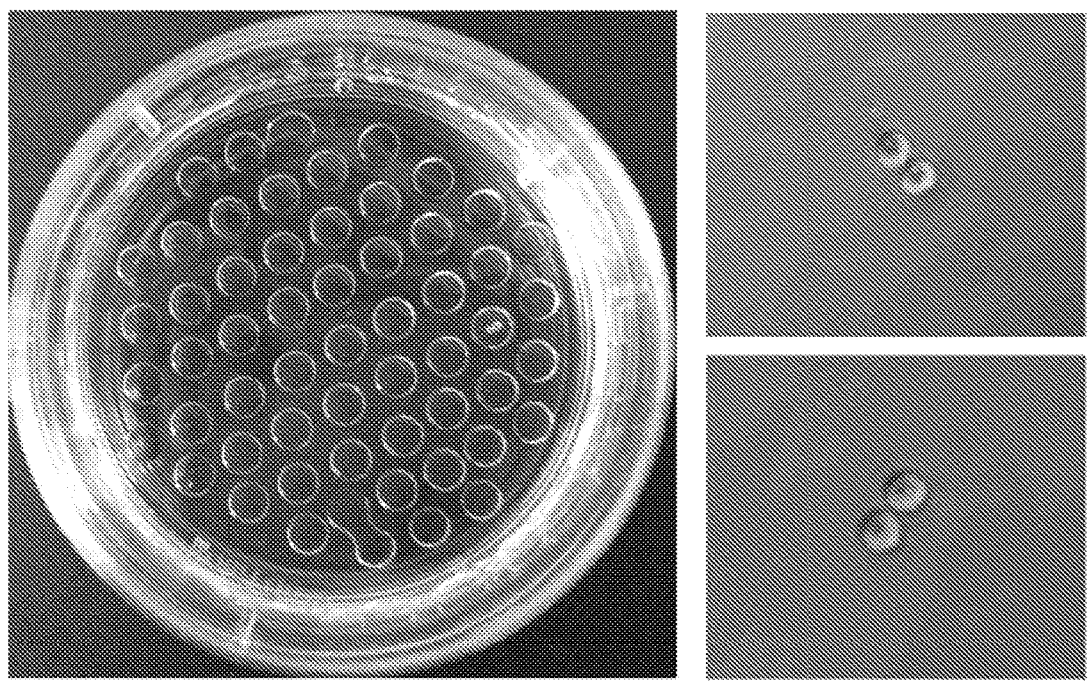
FIG. 9 is a photograph of the derivation of daughter cells after HeLa S3 cell split. The left panel indicates drops containing 2 daughter cells and the right panel represents typical morphology of two daughter cells in each drop.

Correlation analysis showed the telomere lengths between sister cells were proportional by the Pearson test (P=0.005) (FIG. 8B). Telomere lengths between human oocytes and their polar bodies demonstrated no significant differences by the Paired Samples T test, T=0.603, P=0.569, as shown in Table II (FIG. 8C). Occasionally, (e.g. PBI/OI, PB6/O6 specimens) polar bodies and oocytes exhibited different telomere lengths, which could represent degeneration in telomere DNA or biological differences between the cell types. Curiously telomere lengths of oocytes 6 and 7 their polar bodies were remarkably longer than those of other oocytes and polar bodies as determined by one-way ANOVA test, P=0.000 (FIG. 8C). The telomere lengths of human oocytes correlated highly with that of their paired polar bodies telomere lengths by liner correlation analysis (FIG. 8D). Measurements of telomere length in pairs of human oocytes and polar bodies by SCT-pqPCR agreed with previous studies performed by the inventors (23). FIG. 9 shows the culturing of daughter cells resulting from a single cell selection from a HeLa population. Unlike sister cells of mouse two-cell embryos, telomere lengths between daughter cells of HelaS3 frequently showed differences. The correlation between telomere length in daughter cells, however, was still high as presented in Table II (FIGS. 8E and F).

Based on these results, a linear relationship was demonstrated between average T/R values generated with SCT-pqPCR and absolute telomere length generated by TRF, QFISH and conventional qPCR. SCT-pqPCR shows that the average telomere length and its variation within multiple single cells for human lung fibroblasts, embryos and cancer cells, correlate with data obtained by conventional qPCR and QFISH with the corresponding populations of cells.

Example 4: Identification of Telomere Length and its Heterogeneity in Single Cells Via SCT-pqPCR Method Cell and Embryo Culture:

All human samples were collected from consented patients in accordance with the Internal Review Board of New York University Langone Medical Center. Clinical discarded germinal vesicle (GV) stage oocytes were incubated for 24 hours in Human Tubal Fluid (HTF, Irvine Scientific) supplemented with 6% serum plasma supplement (Sage, Quinn's Advantage SPS).

Results

Figure 10B:
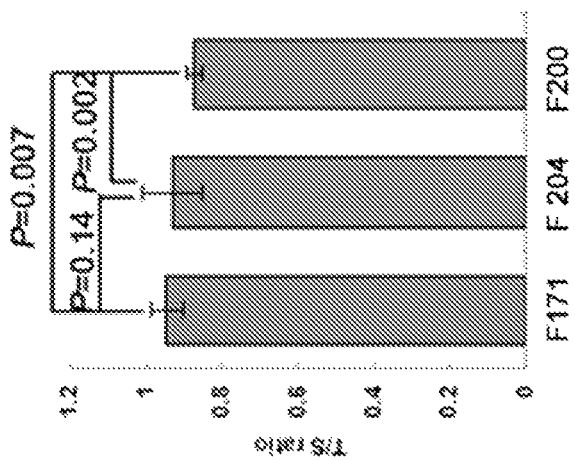
FIGS. 10A and 10B show the telomere length measurement of primary human cell populations as determined by QFISH and regular qPCR.
Figure 10A:
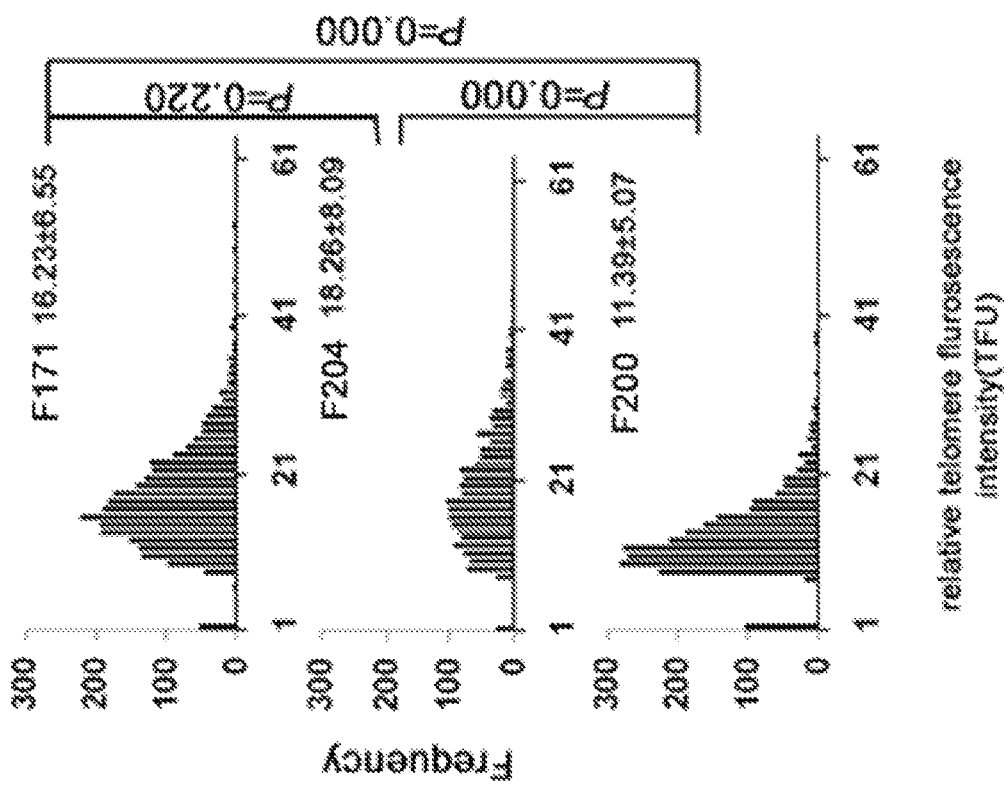

SCT-pqPCR was used to measure the telomere lengths of human lung fibroblast cell lines from different age donors and passage numbers. The average telomere length of human fibroblast cell F171 P16 (gestation at week 14, passage 16) and F204 P14 (35 year old donor, passage 14) was longer (P<0.05) than that of human fibroblast F200 P7 (71 year old donor, passage 7) as measured by QFISH and conventional qPCR. Interestingly however, the average telomere length between F171 P16 and F204 P14 did not differ (P>0.05) when quantitated by these established assays (FIGS. 10A and B). The single cell telomere lengths of F171 P16 and F200 P7 cells were then analyzed by SCT-pqPCR to reveal that the telomere lengths of single cells differed for F171 P16 and F200 P7 cells in the same population, as above. Some single cells from F200 P7 had longer telomeres than F171 P16, as measured by SCT-pqPCR; this finding was confirmed by QFISH analysis (FIGS. 4, 10A and B). The coefficient of variation (CV) shows that single cell telomere length in F200 P7 was more heterogeneous than F171 P16 cells, as shown in Table III.

TABLE III

Variation of single cell telomere length by
SCT-pqPCR and QFISH in different cell lines

| Cell line | T/R ratio | | | QFISH (fluorescence intensity) | | |
|---|---|---|---|---|---|---|
| | mean | standard Deviation | Coefficient of Variation (CV) | mean | standard Deviation | Coefficient of Variation (CV) |
| F171 P16 | 0.845 | 0.143 | 0.169 | 422.652 | 77.626 | 0.184 |
| F171 P31 | 0.749 | 0.364 | 0.486 | — | — | — |
| F200 P7 | 0.710 | 0.165 | 0.233 | 249.855 | 67.251 | 0.269 |
| F200 P12 | 0.724 | 0.289 | 0.398 | — | — | — |
| RuES2 | 1.274 | 0.299 | 0.234 | 578.253 | 138.486 | 0.239 |
| HelaS3 | 0.680 | 0.200 | 0.294 | 339.530 | 113.267 | 0.334 |
| SaOS2 | 1.202 | 0.291 | 0.242 | 625.677 | 240.469 | 0.384 |
| U2OS | 1.872 | 0.419 | 0.224 | 1550.925 | 468.434 | 0.302 |

When human fibroblasts were continuously cultured to further passages, i.e., F171 from passage 16 to passage 31 and F200 from passage 7 to passage 12, metaphase chromosome spreads were rarely available for analysis of cells in these later passages, presumably due to these cells having undergone senescence and failure divide. SCT-pqPCR demonstrated increased variation in telomere length measurements among cells at later passages as compared to ones at early passages (coefficient of variation 0.486 in F171 P31 and 0.398 in F200 P12 vs. 0.169 in F171 P16 and 0.233 in F200 P7, respectively as shown in FIG. 11A and Table I).

Figure 4A:
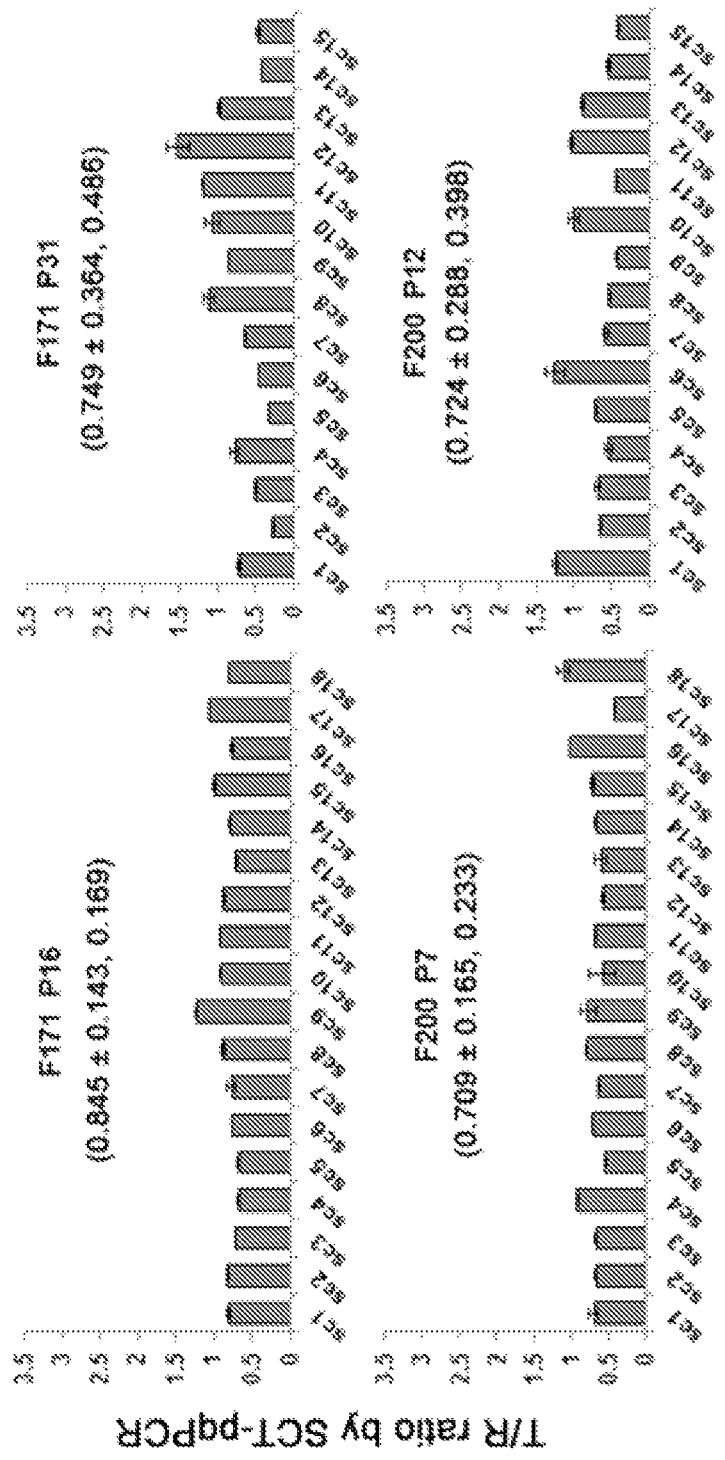
FIGS. 4A-D show the variations of single cell telomere length in different human cell populations by SCT-pqPCR as compared to QFISH.
Figure 4B:
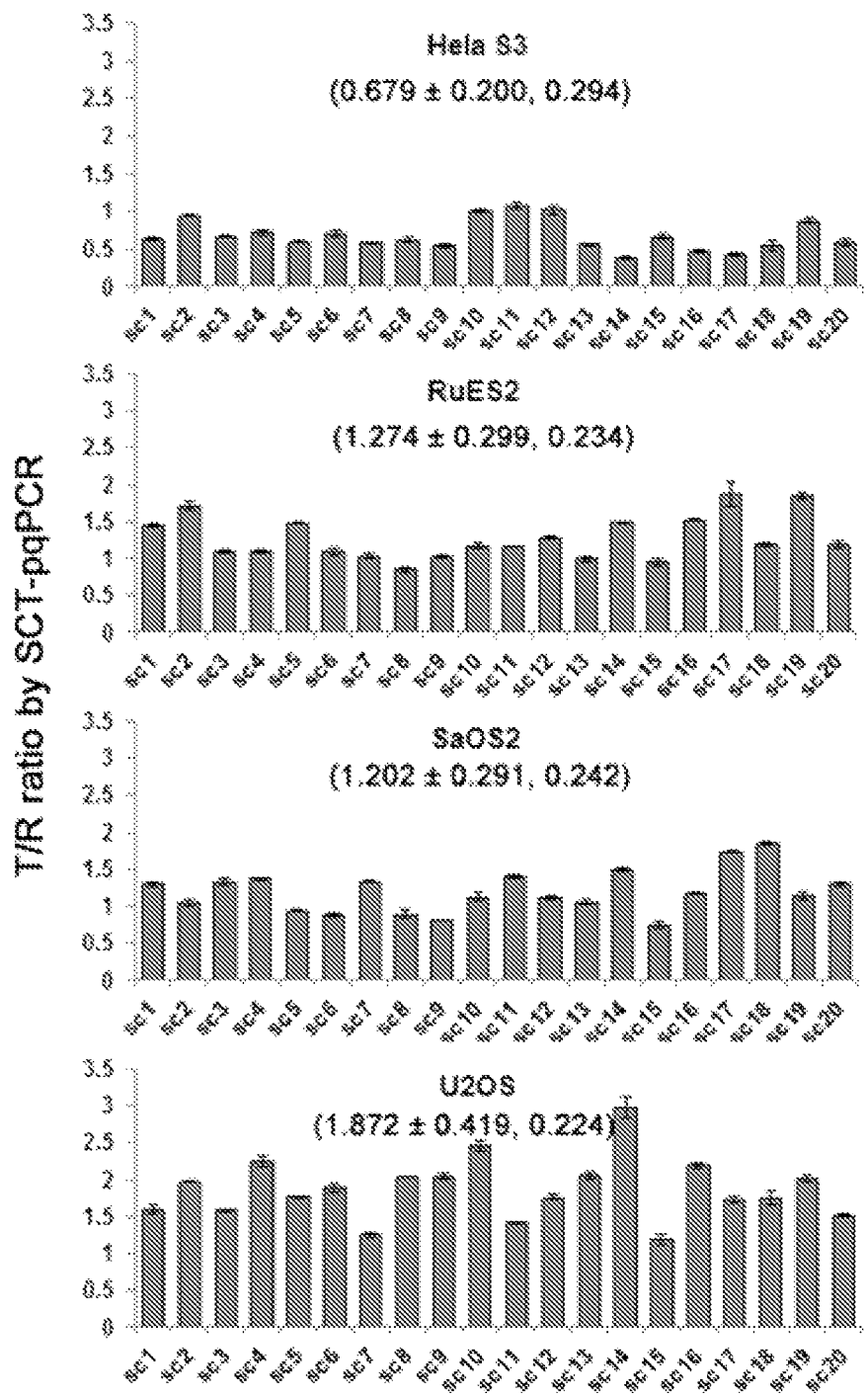
Figure 4C:
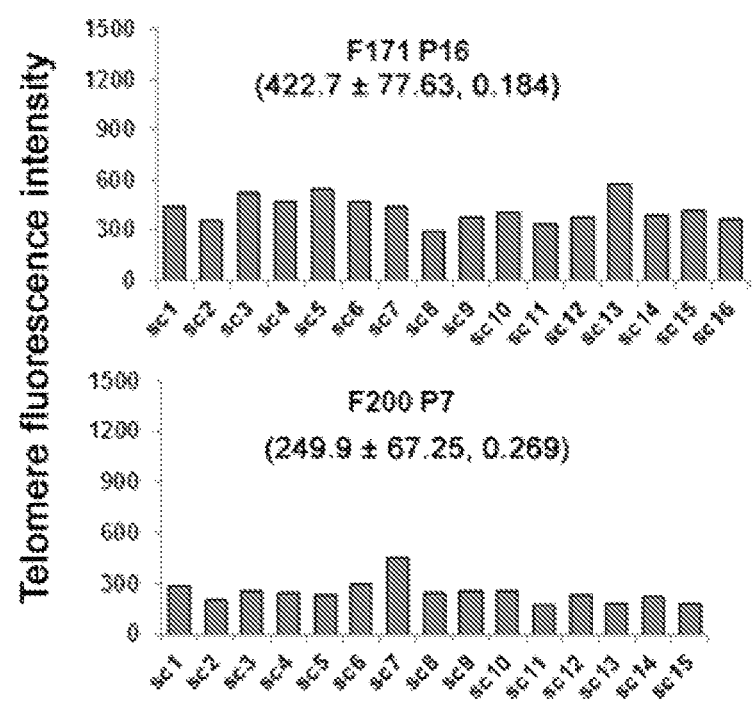
Figure 4D:
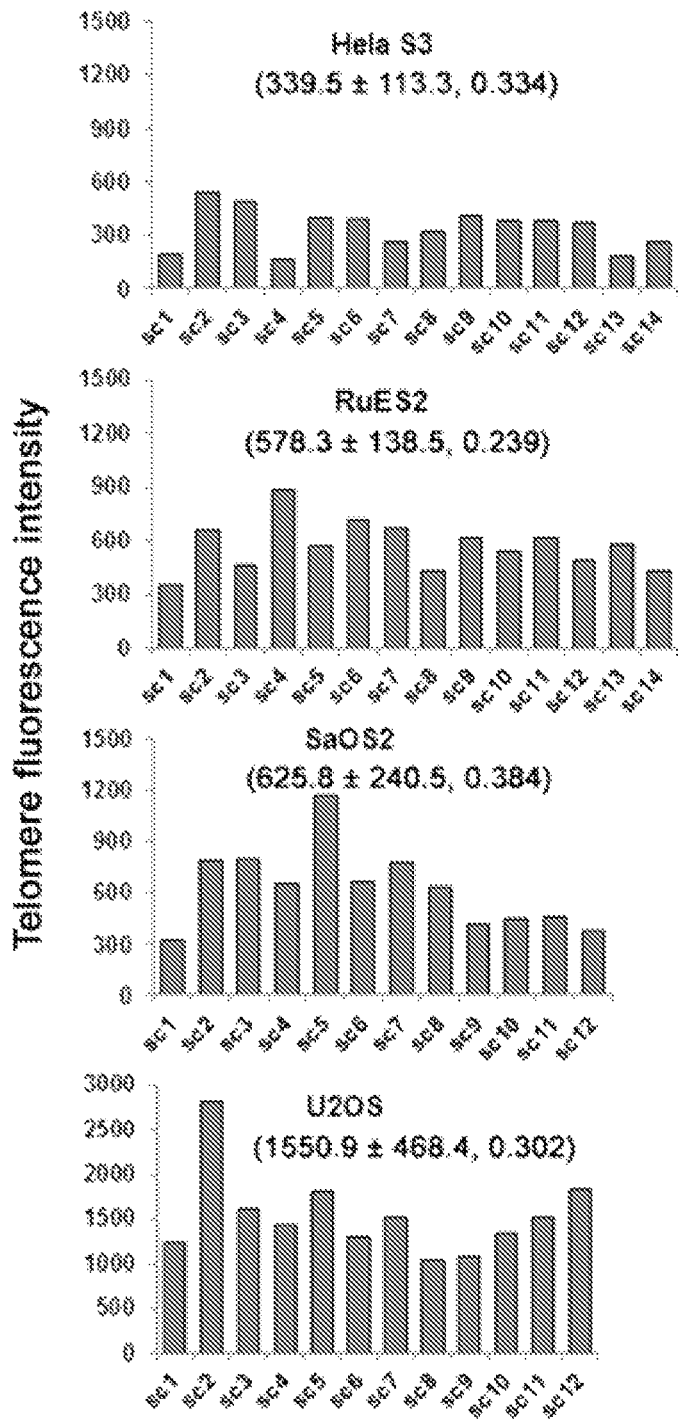

Telomere lengths were also analyzed of single cells having varying telomerase activity from human embryonic stem cell cultures RuES2 (positive telomerase activity), cultured cancer cells HelaS3 (positive telomerase activity) and ALT cells i.e., U2OS and SaOS2 (negative telomerase activity) by SCT-pqPCR. Average telomere length and variability among single cells of a given population differed among these various cell types (FIGS. 4A, C, and 11A). The telomere lengths of individual cells from the HelaS3 culture varied more than the other cell types assayed, with a coefficient of variation of 0.294 (see Table I). The telomere lengths of single cells (HelaS3, Rues2, SaOS2 and U2OS) at metaphase also showed extensive variations when measured by QFISH, confirming that single cell telomere length varies within the same cell population (FIGS. 4B,D and 11B).

The coefficients of variation of different human cell lines as estimated by SCT-pqPCR and QFISH indicate that single cell telomere lengths in cancer cell populations vary more than in early passage human fibroblast cell lines (Table I). Likewise, fibroblasts from older donors show more heterogeneity in telomere length than those of young donors; further cells at later passages show more telomere length variations than those at earlier passages.

Lastly, the telomere lengths of individual cells from mouse zygote to 4-cell embryos were also successfully measured (FIG. 11C). The average telomere length was observed by SCT-pqPCR to be increased together with the developmental stage of the mouse embryos (FIG. 11D). This is consistent with what is known in that telomere length in developing mouse embryos lengthens significantly from the zygote stage to the 4-cell embryo stage (22). Hence, SCT-pqPCR can measure the telomere length with an actual single cell, for example, each sister cell of a 2-cell mouse embryos, which are confirmed identical in T/R ratio.

These aforementioned results present SCT-pqPCR as a simple, efficient and accurate method for measuring differences and heterogeneity in telomere length at the molecular level among individual cells at a resolution comparable to other functional genomics technologies. The above data indicates that telomere length varies among individual cells in a given population. Using this method, the T/R value of early passage human fibroblasts was found to be relatively uniform, but later passages of human fibroblasts and cancer cells become increasingly variable. Further, human oocytes and polar bodies share nearly identical telomere length (T/R), and that the telomere length (T/R) is significantly increased from zygote to 2-cell and to 4-cell embryos. SCT-pqPCR not only allows measurement of telomere length in single cells, independent of their ability to divide, but also provides a tool to estimate the heterogeneity of telomere length in cell populations.

There is a significant advantage in the ability to measure telomere length in individual cells, namely in the understanding and development of therapies for disorders related to telomere shortening. The study identified reliable multi-copy genes, Alu and B1, to normalize telomere measurements. It is possible that aneuploidy may exist in cancer cells and embryos, and single loci may drop out during lysis and pre-PCR. The use of a multi-copy gene also may help avoid such amplification bias from single cells since it targets an abundant sequence, similar to the abundant telomere units, within the single cells. Another unique aspect of the assay is the single-tube pre-amplification of the reference gene in parallel with the telomere sequences for a limited number of cycles by multiplex PCR, which avoids sample loss, and retains a faithful ratio of products, yet significantly expands material for measurements by qPCR. Telomere lengths of the ALT cell SaOS2 by QFISH are longer than those of human ESC (RuES2), which differs from the result obtained by SCT-pqPCR, TRF and regular qPCR. It was found that SaOS2 cells proliferated more slowly. Also, many cells undergo senescence and fail to reach metaphase stage, and thus cannot be measured by QFISH. This heterogeneity may partially explain why telomeres of SaOS2 cells are relatively longer when measured by SCT-pqPCR than by QFISH. These data demonstrate that SCT-pqPCR has an advantage over QFISH for telomere length at single cell levels because it is not dependent on cell division and does not bias results when testing a heterogeneous population of cells consisting of both dividing and quiescent cells.

Such an assay will facilitate the identification and functional studies of cancer stem cells and pluripotent stem cells, and distinguish them from other cells in a mixed populations (24), and advance the understanding of the molecular mechanisms underlying the variation of individual cells in development, disease, senescence and tumorigenesis (25). Single cell telomere estimation also may be particularly useful to predict the viability and chromosomal stability of oocytes and embryos for women undergoing assisted reproductive technologies.

REFERENCES

1. Blackburn E H (2000) Telomere states and cell fates. (Translated from eng) *Nature* 408(6808):53-56 (in eng).
2. Blackburn E H (2001) Switching and signaling at the telomere. (Translated from eng) *Cell* 106(6):661-673 (in eng).
3. Wright W E & Shay J W (2001) Cellular senescence as a tumor-protection mechanism: the essential role of counting. (Translated from eng) *Curr Opin Genet Dev* 11(1): 98-103 (in eng).
4. Gomes N M, et al. (2011) Comparative biology of mammalian telomeres: hypotheses on ancestral states and the roles of telomeres in longevity determination. (Translated from eng) *Aging Cell* 10(5):761-768 (in eng).
5. Marion R M & Blasco M A (2010) Telomeres and telomerase in adult stem cells and pluripotent embryonic stem cells. (Translated from eng) *Adv Exp Med Biol* 695:118-131 (in eng).
6. Lee H W, et al. (1998) Essential role of mouse telomerase in highly proliferative organs. (Translated from eng) *Nature* 392(6676):569-574 (in eng).
7. Aubert G, Hills M, & Lansdorp P M (2012) Telomere length measurement-caveats and a critical assessment of the available technologies and tools. (Translated from eng) *Mutat Res* 730(1-2):59-67 (in eng).
8. Allshire R C, Dempster M, & Hastie N D (1989) Human telomeres contain at least three types of G-rich repeat distributed non-randomly. *Nucleic Acids Res* 17(12): 4611-4627.
9. Cawthon R M (2002) Telomere measurement by quantitative PCR. *Nucleic Acids Res* 30(10):e47.
10. Lansdorp P M, et al. (1996) Heterogeneity in telomere length of human chromosomes. *Hum Mol Genet* 5(5): 685-691.
11. Poon S S, Martens U M, Ward R K, & Lansdorp P M (1999) Telomere length measurements using digital fluorescence microscopy. *Cytometry* 36(4):267-278.
12. Zijlmans J M, et al. (1997) Telomeres in the mouse have large inter-chromosomal variations in the number of T2AG3 repeats. *Proc Natl Acad Sci USA* 94(14):7423-7428.
13. Baerlocher G M & Lansdorp P M (2003) Telomere length measurements in leukocyte subsets by automated multicolor flow-FISH. *Cytometry A* 55(1):1-6.
14. Baird D M, Rowson J, Wynford-Thomas D, & Kipling D (2003) Extensive allelic variation and ultrashort telomeres in senescent human cells. *Nat Genet* 33(2):203-207.
15. Canela A, Vera E, Klatt P, & Blasco M A (2007) High-throughput telomere length quantification by FISH and its application to human population studies. *Proc Natl Acad Sci USA* 104(13):5300-5305.
16. Entringer S, et al. (2011) Stress exposure in intrauterine life is associated with shorter telomere length in young adulthood. (Translated from eng) *Proc Natl Acad Sci USA* 108(33):E513-518 (in eng).
17. Epel E S, et al. (2004) Accelerated telomere shortening in response to life stress. (Translated from eng) *Proc Natl Acad Sci USA* 101(49):17312-17315 (in eng).
18. Dolezel J, Bartos J, Voglmayr H, & Greilhuber J (2003) Nuclear DNA content and genome size of trout and human. *Cytometry A* 51(2):127-128; author reply 129.
19. Dean F B, et al. (2002) Comprehensive human genome amplification using multiple displacement amplification. *Proc Natl Acad Sci USA* 99(8):5261-5266.
20. Pan X, et al. (2008) A procedure for highly specific, sensitive, and unbiased whole-genome amplification. *Proc Natl Acad Sci USA* 105(40):15499-15504.
21. Wang F, et al. (2012) Molecular insights into the heterogeneity of telomere reprogramming in induced pluripotent stem cells. *Cell Res* 22(4):757-768.
22. Liu L, et al. (2007) Telomere lengthening early in development. *Nat Cell Biol* 9(12):1436-1441.
23. Keefe D L, Liu L, & Marquard K (2007) Telomeres and aging-related meiotic dysfunction in women. *Cell Mol Life Sci* 64(2):139-143.
24. Amit M, et al. (2000) Clonally derived human embryonic stem cell lines maintain pluripotency and proliferative potential for prolonged periods of culture. *Dev Biol* 227 (2):271-278.
25. Ma H, et al. (2011) Shortened telomere length is associated with increased risk of cancer: a meta-analysis. *PLoS One* 6(6):e20466.
26. Kimura M, et al. (2010) Measurement of telomere length by the Southern blot analysis of terminal restriction fragment lengths. *Nat Protoc* 5(9):1596-1607.

List of Sequences:

| Primer | Sequence | SEQ ID NO |
|---|---|---|
| Tel-F | CGGTTTGTTTGGGTTTGGGTTTGGGTTTGGGTTTGGGTT | 1 |
| Tel-R | GGCTTGCCTTACCCTTACCCTTACCCTTACCCTTACCCT | 2 |
| m36B4-F | ACTGGTCTAGGACCCGAGAAG | 7 |
| m36B4-R | TCAATGGTGCCTCTGGAGATT | 8 |
| m18srDNA-F | CCAGAGCGAAAGCATTTGCCAAGA | 11 |
| m18srDNA-R | GCATTGCCAGTCGGCATCGTTTAT | 12 |
| mB1-F | GCACCTTTAATCCCAGCAC | 5 |
| mB1-R | TGAGACAGGGTTTCTCTGTA | 6 |
| h36B4-F | CAGCAAGTGGGAAGGTGTAATCC | 9 |
| h36B4-R | CCCATTCTATCATCAACGGGTACAA | 10 |
| h18srDNA-F | CCAGAGCGAAAGCATTTGCCAAGA | 13 |
| h18srDNA-R | TCGGCATCGTTTATGGTCGGAACT | 14 |
| hAlu-F | GACCATCCCGGCTAAAACG | 3 |
| hAlu-R | CGGGTTCACGCCATTCTC | 4 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for determining relative telomere length in a biological sample, which sample comprises less than 20 ng of genomic DNA, said method comprising:
 (a) performing a multiplex pre-amplification of DNA contained in the sample for 12-20 cycles using, in a single reaction mixture, a first primer pair specific for a telomere sequence and a second primer pair specific for a reference sequence, wherein the reference sequence is present in multiple copies in the genome,
 (b) performing a qPCR reaction on the products of step (a) using the first and the second primer pairs, wherein such primer pairs are the same as in step (a) and are present in a single or separate qPCR reaction mixtures,
 (c) calculating a T/R ratio as the ratio of (i) the amount of qPCR product obtained in step (b) using the first primer pair specific for the telomere sequence (T) and (ii) the amount of qPCR product obtained in step (b) using the second primer pair specific for the reference sequence (R), and
 (d) determining the relative telomere length for the sample based on the T/R ratio calculated in step (c), wherein the T/R ratio of more than a standard T/R ratio indicates the relative telomere length greater than normal and the T/R ratio of less than the standard T/R ratio indicates the relative telomere length shorter than normal, wherein the standard T/R ratio is (i) a predetermined value, or (ii) an average T/R ratio for multiple corresponding normal cells, tissues or individuals of the same species, or (iii) a standard curve of T/R ratios for multiple corresponding normal cells, tissues or individuals of the same species.

2. The method of claim 1, wherein the sample comprises less than 10 pg of genomic DNA.

3. The method of claim 1, wherein the sample is a single cell.

4. The method of claim 3, wherein the cell is selected from the group consisting of a polar body, an oocyte, a blastomere, a stem cell, a cancer cell, and a fibroblast.

5. The method of claim 4, wherein the stem cell is an embryonic stem cell.

6. The method of claim 1, wherein the sample is obtained from a human subject.

7. The method of claim 1, wherein the reference sequence is present in more than 1000 copies per genome.

8. The method of claim 1, wherein the reference sequence is a long interspersed repeat or a microsatellite sequence.

9. The method of claim 1, wherein the reference sequence is selected from the group consisting of Alu repeat, B1 repeat and L1 repeat.

10. The method of claim 1, wherein, prior to step (b), the pre-amplification products of step (a) are purified.

11. The method of claim 1, wherein, prior to step (a), the sample is treated with a lysis buffer.

12. The method of claim 1, wherein DNA Polymerase Hot Start Version is used for step (a).

13. The method of claim 1, wherein the first primer pair specific for the telomere sequence is Tel-F (CGGTTT-GTTTGGGTTTGGGTTTGGGTTTGGGTTTGGGTT, SEQ ID NO: 1) and Tel-R (GGCTTGCCTTACCCTTAC-CCTTACCCTTACCCTTACCCT, SEQ ID NO: 2).

14. The method of claim 1, wherein the second primer pair specific for the reference sequence is hAlu-F (GAC-CATCCCGGCTAAAACG, SEQ ID NO: 3) and hAlu-R (CGGGTTCACGCCATTCTC, SEQ ID NO: 4).

15. The method of claim 1, wherein the pre-amplification step (a) is performed using the following sequence of cycles:
 (i) melting at 94° C. for 5 minutes, followed by
 (ii) 16-18 cycles: melting at 94° C. for 15 seconds, annealing at 60° C. for 30 seconds, and extension at 72° C. for 30 seconds, followed by
 (iii) final extension for 10 minutes at 72° C.

16. The method of claim 1, wherein the qPCR step (b) is performed using the following sequence of cycles:
 (i) melting at 95° C. for 10 minutes, followed by
 (ii) 40 cycles: melting at 95° C. for 15 seconds, annealing at 60° C. for 30 seconds, and extension at 72° C. for 30 seconds, followed by
 (iii) 80 cycles of melting curve from 60° C. to 95° C.

17. The method of claim 1, wherein the T/R ratio is determined for two or more different reference sequences simultaneously.

18. The method of claim 1, wherein the amount of qPCR product is determined using a fluorescent label.

19. The method of claim 1, wherein the pre-amplification in step (a) is performed for 16-18 cycles.

20. The method of claim 3, wherein the sample is human and the pre-amplification in step (a) is performed for 17 cycles.

21. The method of claim 3, wherein the sample is murine and the pre-amplification in step (a) is performed for 16 cycles.

22. The method of claim 1, wherein the standard T/R ratio is 1.

23. A method for identifying the presence of a disease involving telomere abnormalities in a biological sample, said method comprising:
 (a) determining relative telomere length in the biological sample using the method of claim 1, and
 (b) identifying the presence of a disease involving telomere abnormalities if the T/R ratio in the biological sample differs from the standard T/R ratio.

24. The method of claim 23, wherein the disease involving telomere abnormalities is selected from the group consisting of cancer, bone marrow failure, pulmonary fibrosis, infertility related to egg dysfunction, precocious aging, and genetic conditions which disrupt normal telomere elongation.

25. The method of claim 23, wherein the sample is a single cell.

26. A method for predicting viability of an oocyte, said method comprising:
(a) determining relative telomere length in a polar body corresponding to the oocyte using the method of claim 1, and
(b) (i) determining that the oocyte has high viability if the T/R ratio in the polar body is similar to the standard T/R ratio, or (ii) determining that the oocyte has low viability if the T/R ratio in the polar body differs from the standard T/R ratio, wherein the standard T/R ratio is an average T/R ratio or a standard curve of T/R ratios for multiple healthy oocytes from healthy oocyte donors.

27. A method for predicting chromosomal stability of an oocyte, said method comprising:
(a) determining relative telomere length in a polar body corresponding to the oocyte using the method of claim 1, and
(b) (i) determining that the oocyte has high chromosomal stability if the T/R ratio in the polar body is similar to the standard T/R ratio, or (ii) determining that the oocyte has chromosomal instability if the T/R ratio in the polar body differs from the standard T/R ratio, wherein the standard T/R ratio is an average T/R ratio or a standard curve of T/R ratios for multiple healthy oocytes from healthy oocyte donors.

28. A method for predicting viability of an embryo, said method comprising:
(a) determining relative telomere length in one or more blastomeres isolated from the embryo using the method of claim 1, and
(b) (i) determining that the embryo has high viability if the T/R ratio in the one or more blastomeres is similar to the standard T/R ratio, or (ii) determining that the embryo has low viability if the T/R ratio in the one or more blastomeres differs from the standard T/R ratio, wherein the standard T/R ratio is an average T/R ratio or a standard curve of T/R ratios of one or more blastomeres from an embryo that created the pregnancy.

29. A method for predicting chromosomal stability of an embryo, said method comprising:
(a) determining relative telomere length in one or more blastomeres isolated from the embryo using the method of claim 1, and
(b) (i) determining that the embryo has high chromosomal stability if the T/R ratio in the one or more blastomeres is similar to the standard T/R ratio, or (ii) determining that the embryo has chromosomal instability if the T/R ratio in the one or more blastomeres differs from the standard T/R ratio, wherein the standard T/R ratio is an average T/R ratio or a standard curve of T/R ratios of one or more blastomeres from an embryo that created the pregnancy.

30. The method of claim 26, wherein the determination of viability or chromosomal stability is conducted in connection with an assisted reproductive technology.

31. The method of claim 27, wherein the determination of viability or chromosomal stability is conducted in connection with an assisted reproductive technology.

32. The method of claim 28, wherein the determination of viability or chromosomal stability is conducted in connection with an assisted reproductive technology.

33. The method of claim 29, wherein the determination of viability or chromosomal stability is conducted in connection with an assisted reproductive technology.

34. The method of claim 11, wherein the lysis buffer comprises 100 mM Tris-HCl pH 7.4, 300 mM NaCl, 0.8 mM EDTA, 2% NP-40, and 5 mM DTT.

* * * * *

SEQUENCE LISTING

<160> NUMBER OF SEQ ID NOS: 14

<210> SEQ ID NO 1
<211> LENGTH: 39
<212> TYPE: DNA
<213> ORGANISM: Artificial Sequence
<220> FEATURE:
<223> OTHER INFORMATION: Primer

<400> SEQUENCE: 1
cggtttgttt gggtttgggt ttgggtttgg gtttgggtt                                  39

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
ggcttgcctt acccttaccc ttacccttac ccttaccct                                  39

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gaccatcccg gctaaaacg                                                        19

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
cgggttcacg ccattctc                                                         18

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
gcacctttaa tcccagcac                                                        19

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tgagacaggg tttctctgta                                                       20

<210> SEQ ID NO 7
<211> LENGTH: 21
<212> TYPE: DNA
<213> ORGANISM: Artificial Sequence

```
<220> FEATURE:
<223> OTHER INFORMATION: Primer

<400> SEQUENCE: 7
actggtctag dacccgagaa g                                          21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tcaatggtgc ctctggagat t                                          21

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
cagcaagtgg gaaggtgtaa tcc                                        23

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
cccattctat catcaacggg tacaa                                      25

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
ccagagcgaa agcatttgcc aaga                                       24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gcattgccag tcggcatcgt ttat                                       24

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
ccagagcgaa agcatttgcc aaga                                       24
```

```
<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
tcggcatcgt ttatggtcgg aact                                              24
```